US011865785B2

(12) United States Patent
Dean et al.

(10) Patent No.: US 11,865,785 B2
(45) Date of Patent: Jan. 9, 2024

(54) CONTINUOUS DIGITAL LIGHT PROCESSING ADDITIVE MANUFACTURING OF IMPLANTS

(71) Applicants: H. David Dean, Shaker Heights, OH (US); Al Siblani, Dearborn Heights, MI (US); Eric J. Mott, Plainwell, MI (US); John P. Fisher, Kensington, MD (US); Martha O. Wang, Columbia, MO (US); Antonios G. Mikos, Houston, TX (US)

(72) Inventors: H. David Dean, Shaker Heights, OH (US); Al Siblani, Dearborn Heights, MI (US); Eric J. Mott, Plainwell, MI (US); John P. Fisher, Kensington, MD (US); Martha O. Wang, Columbia, MO (US); Antonios G. Mikos, Houston, TX (US)

(*) Notice: Subject to any disclaimer, the term of this patent is extended or adjusted under 35 U.S.C. 154(b) by 901 days.

(21) Appl. No.: 15/634,792

(22) Filed: Jun. 27, 2017

(65) Prior Publication Data
US 2018/0126653 A1    May 10, 2018

Related U.S. Application Data

(63) Continuation-in-part of application No. 14/648,446, filed as application No. PCT/US2013/072623 on Dec.
(Continued)

(51) Int. Cl.
*A61L 27/56*    (2006.01)
*B29C 64/386*    (2017.01)
(Continued)

(52) U.S. Cl.
CPC .......... *B29C 64/386* (2017.08); *A61L 27/50* (2013.01); *A61L 27/56* (2013.01); *A61L 27/60* (2013.01);
(Continued)

(58) Field of Classification Search
CPC .......... A61L 27/50; A61L 27/56; A61L 27/60; B29C 64/135; B33Y 30/00; B33Y 50/00;
(Continued)

(56) References Cited

U.S. PATENT DOCUMENTS

| 4,436,684 A | 3/1984 | White |
| 4,976,737 A | 12/1990 | Leake |

(Continued)

FOREIGN PATENT DOCUMENTS

| CN | 101352584 | 3/2013 |
| EP | 2605805 | 2/2012 |

(Continued)

OTHER PUBLICATIONS

C. Sun et al. Projection micro-stereolithography using digital micro-mirror dynamic mask. Sensors and Actuators A, vol. 121 (2005), pp. 113-120 (Year: 2005).*

(Continued)

Primary Examiner — Sanza L. McClendon
(74) Attorney, Agent, or Firm — Renner, Otto, Boisselle & Sklar, LLP

(57) ABSTRACT

A process for additive manufacturing of a resorbable implant to be implanted into a patient includes providing a biocompatible resin including a liquid light-polymerizable material that is resorbable after polymerization and an initiator. The process further includes actuating an additive manufacturing apparatus to expose an amount of the biocompatible resin to light to at least partially cure the exposed amount of biocompatible resin to form a layer of the resorbable implant and actuating the additive manufacturing apparatus to expose at least some additional amount of biocompatible resin to light to at least partially cure the exposed additional amount of biocompatible resin to form an additional layer of the resorbable implant and to at least partially overcure (Continued)

previously cured layers to cause at least some interlayer binding between the previously cured layers and the additional layer.

26 Claims, 14 Drawing Sheets

Related U.S. Application Data 2, 2013, now Pat. No. 10,183,477, and a continuation-in-part of application No. 13/817,612, filed as application No. PCT/US2011/048620 on Aug. 22, 2011, now Pat. No. 9,688,023.

(60) Provisional application No. 61/731,843, filed on Nov. 30, 2012, provisional application No. 61/491,194, filed on May 29, 2011, provisional application No. 61/375,353, filed on Aug. 20, 2010.

(51) Int. Cl.
| | |
|---|---|
| A61L 27/50 | (2006.01) |
| B33Y 30/00 | (2015.01) |
| B33Y 80/00 | (2015.01) |
| A61L 27/60 | (2006.01) |
| B33Y 50/00 | (2015.01) |
| B33Y 70/00 | (2020.01) |
| G03F 7/105 | (2006.01) |
| G03F 7/029 | (2006.01) |
| G03F 7/20 | (2006.01) |
| G03F 7/004 | (2006.01) |
| B29C 64/135 | (2017.01) |
| G02B 26/08 | (2006.01) |

(52) U.S. Cl.
CPC ............ *B33Y 30/00* (2014.12); *B33Y 50/00* (2014.12); *B33Y 70/00* (2014.12); *B33Y 80/00* (2014.12); *G03F 7/0047* (2013.01); *G03F 7/029* (2013.01); *G03F 7/105* (2013.01); *G03F 7/2008* (2013.01); *B29C 64/135* (2017.08); *G02B 26/0833* (2013.01)

(58) Field of Classification Search
CPC .... B33Y 70/00; B33Y 80/00; G02B 26/0833; G03F 7/0047; G03F 7/029; G03F 7/105; G03F 7/2008
See application file for complete search history.

(56) References Cited

U.S. PATENT DOCUMENTS

| | | | |
|---|---|---|---|
| 4,996,010 A | 2/1991 | Modrek | |
| 5,096,330 A * | 3/1992 | Artzberger | E04F 21/248 404/112 |
| 5,182,056 A | 1/1993 | Spence et al. | |
| 5,274,565 A | 12/1993 | Reuben | |
| 5,357,429 A | 10/1994 | Levy | |
| 5,522,019 A | 5/1996 | Bala | |
| 5,554,190 A | 9/1996 | Draenert | |
| 5,647,018 A | 7/1997 | Benjamin | |
| 5,682,886 A | 11/1997 | Delp et al. | |
| 5,741,215 A | 4/1998 | D'Urso | |
| 5,752,962 A | 5/1998 | D'Urso | |
| 5,768,134 A | 6/1998 | Swaelens et al. | |
| 5,813,984 A | 9/1998 | Haaga et al. | |
| 5,871,018 A | 2/1999 | Delp et al. | |
| 6,051,179 A | 4/2000 | Hagenau | |
| 6,071,982 A | 6/2000 | Wise et al. | |
| 6,124,373 A | 9/2000 | Peter et al. | |
| 6,126,690 A | 10/2000 | Ateshian et al. | |
| 6,146,390 A | 11/2000 | Heilbrun et al. | |
| 6,205,411 B1 | 3/2001 | DiGioia, III et al. | |
| 6,206,927 B1 | 3/2001 | Fell et al. | |
| 6,254,639 B1 | 7/2001 | Peckitt | |
| 6,261,493 B1 | 7/2001 | Gaylo et al. | |
| 6,327,491 B1 | 12/2001 | Franklin et al. | |
| 6,415,171 B1 | 7/2002 | Gueziec et al. | |
| 6,445,943 B1 | 9/2002 | Ferre et al. | |
| 6,459,948 B1 | 10/2002 | Ateshian et al. | |
| 6,470,207 B1 | 10/2002 | Simon et al. | |
| 6,500,378 B1 * | 12/2002 | Smith | B29C 35/08 264/401 |
| 6,849,223 B2 * | 2/2005 | Dean | B29C 64/40 264/400 |
| 6,923,817 B2 | 8/2005 | Carson et al. | |
| 6,937,696 B1 | 8/2005 | Mostafavi | |
| 7,747,305 B2 | 6/2010 | Dean et al. | |
| 8,003,040 B2 * | 8/2011 | El-Siblani | A61C 13/0013 264/401 |
| 2001/0027271 A1 | 10/2001 | Franck et al. | |
| 2002/0059049 A1 | 5/2002 | Bradbury et al. | |
| 2002/0123817 A1 | 9/2002 | Clasbrummel et al. | |
| 2002/0171178 A1 | 11/2002 | Dean et al. | |
| 2003/0013080 A1 | 1/2003 | Luebke et al. | |
| 2003/0216669 A1 | 11/2003 | Lang et al. | |
| 2004/0054372 A1 | 3/2004 | Cordon et al. | |
| 2004/0167390 A1 | 8/2004 | Alexander et al. | |
| 2008/0015433 A1 | 1/2008 | Alexander et al. | |
| 2009/0130174 A1 | 5/2009 | Guelcher et al. | |
| 2009/0130449 A1 | 5/2009 | El-Siblani | |
| 2010/0003619 A1 | 1/2010 | Das et al. | |
| 2010/0262272 A1 * | 10/2010 | Shkolnik | B29C 64/393 700/120 |
| 2011/0033887 A1 * | 2/2011 | Fang | C12M 23/16 435/41 |
| 2012/0010711 A1 | 1/2012 | Anthonyshyn et al. | |
| 2012/0072185 A1 | 3/2012 | Lang et al. | |
| 2013/0304233 A1 | 11/2013 | Dean et al. | |

FOREIGN PATENT DOCUMENTS

| | | |
|---|---|---|
| GB | 2324470 | 10/1998 |
| JP | 2010-509090 T | 3/2010 |
| WO | WO 2009/042671 | 11/2002 |
| WO | WO 2012/2024675 | 2/2012 |

OTHER PUBLICATIONS

Armentano, et al., "Biodegradable polymer matrix nanocomposites for tissue engineering: A review, 95 Polymer Degradation and Stability," vol. 95, pp. 2126-2146, Jun. 18, 2010.
Peter, "Injectable in situ polymerizable, biodegradable scaffolds based on poly (propylene fumarate) for guided bone regeneration," PHD Thesis, Rice University, Chapters 1.2 and 2, 1998.
International Search Report and Written Opinion of corresponding International Application No. PCT/US2011/048620, dated Apr. 10, 2012.
International Preliminary Report on Patentability of corresponding International Application No. PCT/US2011/048620, dated Feb. 26, 2013.
Zachow S. et al., "Optimized arrangement of osseointegrated implants: a surgical planning system for the fixation of facial prostheses" Proceedings of 13th International Symposium on Computer Assisted Radiology and Surgery (Cars '99), Paris, France, Jun. 23-26, 19999, pp. 942-946, XP001011404 1999, Amsterdam, Netherlands, Elsevier Science, Netherlands ISBN: 0-444-50290-4 (previously cited in U.S. Appl. No. 10/129,308, filed Sep. 3, 2002).
Noordmans H. J. et al., "Localisation of subdural EEG electrode bundles in an interactive volume Rendering framework" Medical Image Computing and Computer-Assisted Intervention-Miccai '99, Second International Conference, Proceedings (Lecture Notes in Computer Science vol. 1679), Cambridge, UK, Sep. 19-22, 1999, pp. 734-741, XP0010113911999, Berlin, Germany, Springer-Verlag, Germany, ISBN: 3-540-66503-C=X, abstract (previously cited in U.S. Appl. No. 10/129,308, filed Sep. 3, 202).

(56) References Cited

OTHER PUBLICATIONS

Wells W. et al., "Video Registration Using Fiducials for Surgical Enhanced Reality" Proceedings of the Annual International Conference of the Engineering in Medicine and Biology Society, US, New York, IEEE, vol. CONF. 15, Oct. 28, 1993 (Oct. 28, 1993), pp. 24-25, XP000431483 (Previously cited in U.S. Appl. No. 10/129,308, filed Sep. 3, 2002).
Article entitled "Biomedical applications" found at http:\\www.ifi.unizh.ch/staff/zolli/cap/biomedical.htm.
Dean H.D. et al., "Comparison of Traditional Brain Segmentation Tools with 3D Self-Organizing Map".
Sailerh.F. et al., "The value of stereolithographic models for pre-operative diagnosis of craniofracial deformities and planning of surgical corrections," Int. J. Oral Maxillofac, Surg. 1998,27, 327-333 ISSN 0901-5027.
Office Action of corresponding Mexican Application No. MX/a/2013/002049, dated Dec. 19, 2017.
Neumeister et al., "Process accuracy during laser-based stereolithography", Proceedings of the 3nd International Conference on Advanced Research in Virtual and Rapid Prototyping, Leiria, Portugal, Sep. 24-29, 2007, London [u.a], (Dec. 31, 2008), pp. 502-505.
J. Rieker et al., "Recent Developments in Radical Photoinitiator Chemistry", Chimia, vol. 48, (Sep. 30, 1994), pp. 423-426.
Office Action of corresponding Korean Application No. 10-2013-7007101, dated Nov. 16, 2017.
Lu, Y. et al., "A digital micro-mirror device-based system for the microfabrication of complex, spatially patterned tissue engineering scaffolds", Journal of Biomedical Materials Research. Part 1, vol. 77, No. 2, pp. 396-405. ISSN: 1549-3296.
Office Action of corresponding Japanese Application No. 2013-526067, dated Apr. 6, 2015.
Office Action of corresponding Japanese Application No. 2013-526067, dated Oct. 27, 2015.
Office Action of corresponding Japanese Application No. 2013-526067, dated Feb. 22, 2016.
Written Opinion of corresponding International Application No. PCT/US2011/048620, dated Apr. 10, 2012.
European Search Opinion of corresponding International Application No. 11 818 890.3, dated Jul. 13, 2017.
Office Action of corresponding Chinese Application No. 201180049086.1, dated Mar. 25, 2014.
Office Action of corresponding Chinese Application No. 201180049086.1, dated Feb. 2, 2015.
Office Action of corresponding Canadian Application No. 2,808,535, dated Sep. 14, 2015.

\* cited by examiner

CONTINUOUS DIGITAL LIGHT PROCESSING ADDITIVE MANUFACTURING OF IMPLANTS

CROSS REFERENCE TO RELATED APPLICATIONS

This application is a continuation-in-part of U.S. patent application Ser. No. 13/817,612 filed on Jul. 26, 2013 which is a National Stage entry of PCT/US2011/048620 filed on Aug. 22, 2011, which claims the benefit of U.S. Provisional Patent Application Nos. 61/373,353 filed on Aug. 20, 2010 and 61/491,194 filed on May 29, 2011, which are incorporated herein by reference. This application is also a continuation-in-part of U.S. patent application Ser. No. 14/648,446 filed on May 29, 2015, which is National Entry of PCT/US2013/072623 filed on Dec. 2, 2013, which claims the benefit of U.S. Provisional Patent Application No. 61/731,843 filed on Nov. 30, 2012, which are incorporated herein by reference.

FEDERAL FUNDING NOTICE

This invention was made with government support under grant numbers R01-DE013740 and R01-AR061460 awarded by the National Institutes of Health (NIH). The government has certain rights in the invention.

BACKGROUND

Tissue engineering is an attempt to regenerate a defect in tissue that is larger than the unaided body can regenerate on its own. In most cases tissue engineering requires technology for the creation of three components: implants (often referred to as scaffolds), cells and growth factors. Tissue regeneration not only requires the infusion of cells specific to the function of the organ but also vasculature and often connective tissue. Growth factors can aid in the performance of concentrated tissue precursor cells or the recruitment of reparative host tissue. Implants or scaffolds are often required to provide guidance to stem cells and/or invading host tissue, vasculature and connective tissue. Implants may be designed to match a defect in a patient's tissue. The shape of the implant may be determined by first measuring the defective area or volume within the patient. The implant may then be designed by, for example, computer aided design (CAD) in light of the measured defective area or volume. The implant may then be manufactured.

Factors to take into account when designing and manufacturing implants include adequate geometry to provide a proper fit: (a) the external surface fit of the implant into the defect site, and (b) the porous space within an implant to guide the initial infusion of tissue, vasculature, and connective tissue. If the walls between porous spaces of the implant or scaffold are too thick they may not resorb, and thereby become a barrier to remodeling. If the materials degrade, their byproducts need to be non-toxic and easily metabolized so that they do not prevent tissue regeneration or remodeling.

Functional geometrical features of a scaffold may be designed to affect cell attachment, proliferation, or maturation. Surface features that interact directly with cells include scaffold roughness and porosity. Rough, porous structures may facilitate cell loading, neotissue growth, and host tissue ingrowth. The designer may manipulate porous geometry to control both the mechanical properties of the whole implant as well as the pore space's porosity, tortuosity, permeability, and total pore volume. Many tissue engineering scaffolds may require pores that range between 200 and 1600 micrometers with varying surface features, such as the shape of the pore opening, in the order of 50-500 micrometers. Conventionally, these features may have been obtained by the inclusion of particles such as tricalcium phosphate crystals into the resin from which the scaffold would be manufactured. However, concerns may arise as to the resorbability of the crystals in the host's body.

Another important geometrical feature may be oblique orientation of pore structures in order for the host tissue to not encounter a wall or barrier in the scaffold, which is more likely when pore structures are built orthogonally than when pores or channels are oriented towards host tissue. The implant designer may want to orient pores channels within a scaffold so that they open toward the host tissue thereby facilitating growth of new tissue into the implant and active incorporation of the implant into the host tissue.

Additive manufacturing of implants or scaffolds with these mechanical and geometrical features requires relatively high accuracy levels. For example, accurate rendering makes it more likely that complex internal pore structures such as those described above and other can be created. Stereolithography is described by Paul Jacobs in: Rapid Prototyping & Manufacturing: Fundamentals of Stereo-Lithography by Paul F. Jacobs (Jan. 15, 1992), and Stereolithography & Other RP&M Technologies: From Rapid Prototyping to Rapid Tooling by Paul F. Jacobs (Jan. 1, 1996).

Additional factors to take into account when designing and manufacturing implants or scaffolds are adequate strength and stiffness for the part to handle and transmit mechanical stress. In some cases, strength and stiffness must be weighed against the need for the implant or scaffold to be resorbable or capable of breaking down in the host's body. Manipulation of the polymer's molecular weight often adjusts both the rate and extent of resorption levels in vitro as well as in vivo versus strength of the implant, with higher molecular weights often being stronger and lower molecular weights often being more resorbable. However, post-curing handling of low molecular weight scaffolds or implants could be problematic and thus the ideal rendering method would minimize any post-curing handling necessary.

While stereolithographic rendering of implants and scaffolds has been demonstrated, limitations in the commercially available devices has thus far resulted in relatively low accuracy levels.

For example, accuracy and resolution of conventional stereolithographic rendering devices may not allow the devices to produce scaffold or implant surface features such as pores and pore openings at the low end of the optimum geometry scale. While conventional stereolithographic rendering devices may be able to produce orthogonally oriented pore structures in implants and scaffolds, they may not be able to provide sufficient resolution to produce obliquely oriented pores. Moreover, stereolithographic rendering may also have various other limitations in the context of manufacturing of implants or scaffolds. For example, conventional stereolithography devices use a laser to polymerize layers. The laser points downward at the top of a vat of liquid polymer. An elevator sits inside the vat and pulls the part downward as it is rendered, layer by layer. The drawing speed is typically not fast enough to simultaneously draw all pixels in the layer, which may make it difficult to control pixel to pixel crosslinking within the layer and/or over-curing or stitching between layers as the implant or scaffold is rendered.

Also, conventional stereolithography devices may not provide a way to modulate the amount of energy at one spot versus another within a layer to, for example, control the depth of polymerization and level or strength of over-curing. Controlling the depth of polymerization as well as the level or strength of curing is critical.

Control of resolution in chain length dependent propagation with continuous digital light processing ("cDLP") as in many other forms of photo-initiated additive manufacturing is essential to render useful and accurate parts. Several important technological aspects that allow for highly accurate additive manufacturing are (i) accurate delivery of light, (ii) good control of the wavelength and amount of energy in that light, and (iii) a build surface that can be moved into an appropriate position to form each layer and have it bind (i.e. laminate) with the previously built layer.

Normally, in cDLP manufacturing, light inhibiting agents, known as dyes (also referred to as light attenuators), are introduced to a polymer mixture in order to limit the wavelengths of light that activate a photo-initiator as a means to control the depth of curing, or the z-axis resolution. These dyes are numerous, however, the selection of biocompatible ones are much less. Furthermore, dyes that are effective against ultraviolet transmission and USP grade are even harder to come by. One dye that fits these requirements is titanium dioxide. Like many ceramics, it is biocompatible, stable, and small in particle size, making it ideal for use in photo-initiated polymer mixtures. However, in its effectiveness, there is an inevitable downside, while titanium dioxide is a strong ultraviolet absorber, it also has strong scattering properties, which leads to inadvertent curing, thereby decreasing resolution in the xy-plane and potentially z-plane as well. This phenomenon is called "dark-cure." Identification of dyes or other biocompatible agents that function together with titanium dioxide, as well as on their own to produce resorbable, biocompatible tissue engineering scaffolds with desired physical, biological and chemical properties are needed.

SUMMARY OF THE INVENTION

Disclosed herein are compositions for light-polymerizable resin mixtures used in 3D manufacturing resorbable scaffolds and implants (tissue engineering). The term resin is used herein to refer to light-polymerizable flowable material (e.g. liquid) contains polymer, and other constituents such as dye, photo-initiator, etc. and is used in additive manufacturing applications. As used herein, the terms percent (%) weight or weight by weight ("w/w") are used interchangeably.

Resolution of an additive manufactured part is controlled in a light-polymerizable resin composition by the use of a first substance in the resin composition that controls between plane (z) resolution of the manufactured part, a photo-initiator and a second substance which controls within plane (x-y) resolution of the manufactured part.

A dye-initiator package for a resin composition used in the additive manufacturing of resorbable implants comprises a dye which limits the transmission of light that activates a photo-initiator, a photo-initiator and a light absorber which absorbs light reflected from the first dye. According to one embodiment, the first dye is $TiO_2$. According to a separate embodiment, the photo-initiator is an acylphosphine oxide. According to a separate embodiment, the light absorber is a benzophenone. According to yet another embodiment the photo-initiator is Bis(2,4,6-trimethylbenzoyl)-phenylphosphineoxide (BAPO). According to yet another embodiment, the light absorber is oxybenzone (2-Hydroxy-4-methoxybenzophenone), also known as "HMB".

A dye-initiator package for a resin composition used in the additive manufacturing of resorbable implants comprises, a first dye which limits the transmission of light that activates a photo-initiator, a photo-initiator and a light absorber which absorbs light reflected from the first dye. According to one embodiment, the first dye is Bis(.eta.5-2,4-cylcopentadien-1-yl)-bis(2,6-difluoro-3-(1H-pyrrol-1-yl)-phenyl) titanium (Irgacure® 784). According to a separate embodiment, the photo-initiator is Bis(2,4,6-trimethylbenzoyl)-phenylphosphineoxide (BAPO). According to yet another embodiment, the light absorber is oxybenzone (2-Hydroxy-4-methoxybenzophenone), a dibenzoylmethane or a photostable derivative thereof (e.g. avobenzone), octinoxate, octocrylene or padimate O.

A dye-initiator package for a liquid light-polymerizable composition used in the manufacturing of resorbable scaffolds and implants comprises a dye, a photo-initiator and a light absorber, wherein the dye is about 0.1 to about 5.0% $TiO_2$ weight by weight of the liquid light-polymerizable composition (w/w), the photo-initiator is about 0.1 to about 5.0% (w/w) BAPO, and the light absorber is about 25 to about 35% (w/w) oxybenzone wherein the denominator is the weight of the liquid light-polymerizable polymer(s) and any solvent used in the composition or resin. In another embodiment, the dye is about 0.1 to about 5.0% Bis(.eta.5-2,4-cylcopentadien-1-yl)-bis(2,6-difluoro-3-(1H-pyrrol-1-yl)-phenyl) titanium by weight, the photo-initiator is about 0.1 to about 5.0% BAPO by weight, and the light absorber is about 0.1 to about 5% oxybenzone by weight.

A dye-initiator package for a resin composition used to manufacture resorbable scaffolds and implants comprises first dye and a photo-initiator, wherein the first dye comprises Bis(.eta.5-2,4-cylcopentadien-1-yl)-bis(2,6-difluoro-3-(1H-pyrrol-1-yl)-phenyl) titanium and the photo-initiator comprises Bis(2,4,6-trimethylbenzoyl)-phenylphosphineoxide (BAPO). According to one embodiment, the composition includes about 0.1-5.0% (w/w) of the first dye and about 0.1-5.0% (w/w) of the photo-initiator, wherein the weight percents are based on the weight of the polymer(s) and any solvent used in the resin. Other ranges include about 0.1-1% (w/w) for the first dye and about 1-3% (w/w) for the photo-initiator.

A photo-initiator package for a liquid light polymerizable composition for use in tissue engineering applications comprises a first photo-initiator and a second photo-initiator wherein the first photo-initiator cures the composition when exposed to a first light source in an additive manufacturing device and the second photo-initiator limits the transmission of light that activates the first photo-initiator in the additive manufacturing device, and wherein the second photo-initiator is activated when exposed to a second light source used to post-cure the composition. In one embodiment, one or both of the first and second photo-initiators are an acylphosphine oxide. According to yet another embodiment, the first photo-initiator is BAPO and the second photo-initiator is Bis(.eta.5-2,4-cylcopentadien-1-yl)-bis(2,6-difluoro-3-(1H-pyrrol-1-yl)-phenyl) titanium. Also contemplated herein is a method of increasing the strength of a 3D printed tissue engineering part comprises mixing a light-polymerizable polymer with a first photo-initiator and a second photo-initiator, wherein the second photo-initiator limits the transmission of light that activates the first photo-initiator, exposing the mixture to localized light to cure the polymer, and post-curing the product in a light bath, wherein the light in the light bath activates the second photo-initiator to increase the strength of the manufactured part.

A dye-initiator package for an additive manufacturing resin comprising a first dye, a photo-initiator, a light absorber, and optionally, a second dye. The dyes can be titanium dioxide and/or Bis(.eta.5-2,4-cylcopentadien-1-yl)-bis(2,6-difluoro-3-(1H-pyrrol-1-yl)-phenyl) titanium (Irgacure® 784). The photo-initiator can be Bis(2,4,6-trimethylbenzoyl)-phenylphosphineoxide (BAPO). The light absorber can be oxybenzone (2-Hydroxy-4-methoxybenzophenone). In one embodiment, the package comprises about 0.1-5% (w/w) $TiO_2$, about 0.1-5% (w/w) BAPO, about 0.1-5% (w/w) Irgacure® 784, and about 8-15% (w/w) oxybenzone wherein the weight percents are based on the weight of the polymer(s) and any solvent used in the resin.

A liquid light-polymerizable composition for use in additive manufacturing of resorbable implants comprising a biocompatible polymer, a solvent, and a dye-initiator package. According to one embodiment, the biocompatible polymer comprises polypropylene fumarate, the solvent comprises diethyl fumarate, and the dye-initiator package comprises a dye, a photo-initiator, a light absorber and optionally a second dye.

A liquid light-polymerizable composition for 3D printing of biocompatible, resorbable scaffolds, comprising a biocompatible polymer, a solvent, and a dye-initiator package, wherein the biocompatible polymer comprises polypropylene fumarate, the solvent comprises diethyl fumarate, and the dye-initiator package comprises a dye and a photo-initiator. The composition may comprise a weight ratio of polypropylene fumarate to solvent in a ratio of 1:1, 1.5:1, 2:1 or 3:1, about 0.1-5.0% (w/w) dye wherein the weight percent of the dye is based on the weight of polypropylene fumarate and solvent in the composition, and about 0.1-5.0% (w/w) photo-initiator wherein the weight percent of the photo-initiator is based on the weight of polypropylene fumarate and solvent in the composition. The composition further comprises a light absorber in the range of about 10-35% (w/w) wherein the weight percent of the light absorber is based on the weight of polypropylene fumarate and solvent in the composition. The composition further comprises a second dye in the range of about 0.1-5.0% (w/w).

DETAILED DESCRIPTION

Additive Manufacturing

Figure 1:
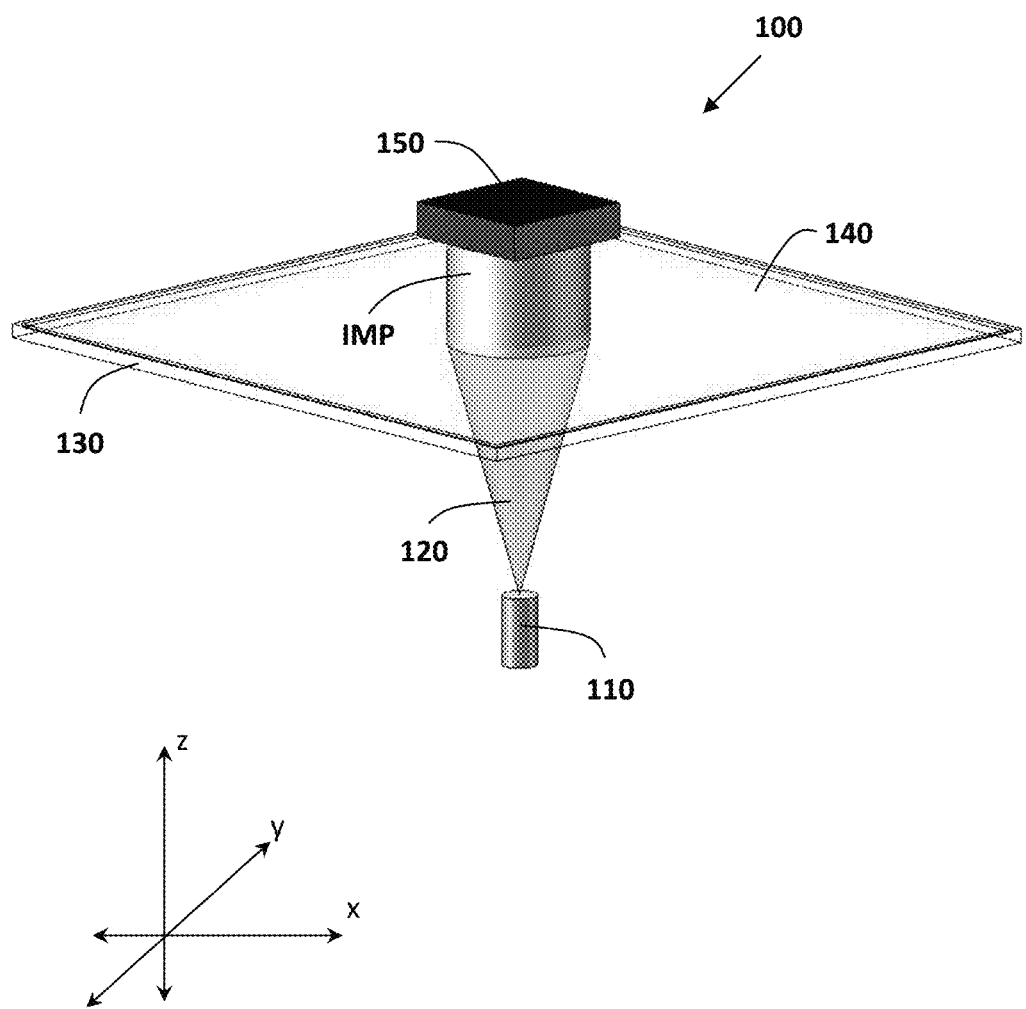
FIG. 1 illustrates a continuous digital light processing (cDLP) device for the additive manufacturing of an implant.

FIG. 1 illustrates a continuous digital light processing (cDLP) device 100 for the additive manufacturing of an implant IMP. The device 100 includes a digital micro-mirror device (DMD) projector 110. A DMD consists of an array of micro-mirrors which controls the intensity of projected light in each pixel of the layer image, effectively polymerizing each voxel (volumetric pixel) of each layer of the implant IMP. The term "continuous" in continuous digital light processing (also referred to as "micro-stereolithography", "projection stereolithography" or "projection printing") indicates that all voxels within a layer can be projected simultaneously, as opposed to the successive drawing (i.e., moving of laser beam) of voxels that occurs in other additive manufacturing methods such as stereolithography. cDLP based additive manufacturing projects multiple voxels that may add up to a complete implant layer as one image, or "voxel mask." This allows for the entire layer to be cured simultaneously (i.e., continuous curing).

Other 3D printing techniques that rely on photocrosslinking are also contemplated herein, and the resin compositions contemplated herein apply to traditional stereolithography as well as two-photon fabrication, which can achieve submicron accuracy and other 3D printing techniques that rely on photocrosslinking.

The projector 110 projects light 120 through a transparent or translucent basement plate 130 above which is a resin 140 including a liquid light-polymerizable material. Exposure to the light 120 causes the resin 140 to at least partially cure or polymerize to form layers of the implant IMP. In the illustrated embodiment, the device 100 further includes a build plate 150 to which the implant IMP operatively attaches. The build plate 150 operatively attaches to a motor (not shown), the operation of which successively shifts or elevates the build plate 150 away from the basement plate 130 as the light 120 successively cures or polymerizes the resin 140 to form each layer of the implant IMP. The light 120 further polymerizes or overcures previously rendered layers to bind or stitch newly polymerized layers to the previous layers.

In one embodiment, the cDLP device 100 is the Perfactory® UV device produced by envisionTEC (Gladbeck, Germany). In another embodiment, the cDLP device 100 would be a cDLP device other than the Perfactory® UV device produced by envisionTEC.

Accuracy and Resolution

Accuracy in 3D printing strategies depends on the hardware supporting the delivery of light, the resin chemistry that responds to that light, as well as the accuracy of build platform positioning during layer-by-layer fabrication. Photocrosslinking-based 3D printing techniques may have the highest accuracy among all additive manufacturing modalities.

In one embodiment, each projected voxel mask also uses spatially varying irradiance, meaning that each pixel may be assigned a different light intensity value. Benefits of assigning each pixel a different intensity value include, the ability of varying curing rates within a layer and allowing for anti-aliasing methods analogous to those found in image processing. In one embodiment, the cDLP device 100 is equipped with an Enhanced Resolution Module (ERM) (not shown) which effectively doubles the within-layer (x-y) resolution through a process similar to pixel shifting, a technique which increases the true resolution of devices by moving the micro-mirrors by fractions of a pixel in the x and y directions.

The unique properties of cDLP rendering allow for improved accuracy defined as the similarity of the resulting implant or scaffold to the shape found in the design, or CAD, file. One source of increased accuracy is in-plane (x-y) resolution, which is a function of the projector lens magnification and the resolution of the DLP chip. Pixel sizes may be 75 micrometers or less. ERM, pixel shifting, anti-aliasing, or combinations thereof may further increase the in-plane resolution by at least a factor of 2.

The cDLP device 100 further provides increased accuracy due to increased between-plane or (z) resolution. The between-plane (z) resolution is controlled by, among other factors, the motor (not shown), which shifts the build plate 150 between serial layers. In one embodiment, the device 100 has a motor capable of increments of 50 micrometers and as small as 15 micrometers. The between-plane (z) resolution may be further controlled by controlling the depth of penetration of the light 120 to limit polymerizing energy into the resin 140 or previously rendered layers of the implant IMP.

Accuracy in the resolution of the implant or scaffold is also determined by the components of the resin, which may be manipulated to improve the accuracy of where the polymer will be photo-crosslinked, and the cross-linking density. Controlling the cross-linking may increase the accuracy of the rendered implant surface, allow control of material properties within the implant, where light can be used to create inhomogeneous distribution of cross-link density, and decrease the amount of handling needed during the fabrication process if the resolution of the polymerization is improved.

A model of the Perfactory® UV device has a motor capable of increments of 50 micrometers and a 60 millimeter lens, providing an in-plane (x-y) native resolution of 71 micrometers and 35.5 micrometers utilizing pixel shifting. Thus this model of the Perfactory® UV device is capable of continuously polymerizing 35.5×35.5×50 µm voxels. Another model of the Perfactory® UV device would have a 75 millimeter lens that would provide a 42 micrometer native in-plane (x-y) resolution and 21 micrometers resolution with pixel shifting.

Light-Polymerizable Material

The cDLP process controls mechanical and other properties of the resulting implant IMP, in part, by controlling the molecular weight of the light-polymerizable material. Manipulation of the material's molecular weight adjusts the strength of the resulting implant IMP, with higher molecular weights generally being stronger. Thus, for applications where the implant IMP would bear significant mechanical stress, the light-polymerizable material may be chosen such that the rendered part may adequately handle and transmit the mechanical stress.

In applications such as implants or scaffolds, which are intended for implantation in a patient's body, it is important that components of the implant or scaffold including the light-polymerizable material as well as any initiators, dyes, solvents, and other substances be biocompatible, meaning that the implant poses no substantial risk of injury or toxicity to living cells, tissues, or organs, and poses no substantial risk of rejection by the immune system. In some instances, it is possible to use some non-biocompatible components or processes. However, they would usually be fully removed or rendered biocompatible prior to implantation. For example, some non-biocompatible chemicals may be used during the manufacturing process, but should be fully removed before implantation.

In applications such as tissue engineering scaffolds, resorbability or bioabsorbability of the scaffold, the ability of the part to break down in the host's body, is a very important consideration. It is important to the regeneration of tissue such as bone that the scaffold resorb in response to cell maturation and incoming host tissue. Well-timed scaffold resorption is important for successful integration of vasculature to allow unfettered remodeling and host incorporation of neotissue. Thus, predictable scaffold resorption is important including predictable rates of loss of material properties, predictable rates of scaffold degradation (e.g., it may be useful to choose polymers that fracture or erode at predictable rates rather than bulk degrade), and predictable rates pH change. A wide range of biocompatible polymers exist, including poly (1) lactic acid PLA), poly(glycolic) acid (PGA), Poly(ε-caprolactone). Vert Bioabsorbable polymers in Medicine—an overview. Eurointervention Supplement (2009) (5)(F): F9-F14.

It may also be advantageous to incorporate antibiotics and bioactive molecules in scaffold resin. The incorporation of bioactive ligands may be useful to promote selective attachment of cells useful to the neotissue (e.g. osteoblasts in bone scaffolds) and selective attachment of certain cells may be preferential to over undesirable cell types. Ligands may also be used that upregulate a cellular component relevant to cell attachment, improve proliferation of attached cells, and or promote subsequent maturation of cells toward the desired tissue function.

Strength and stiffness of the scaffold must be weighed against rates of resorbability of the scaffold. Manipulation of the material's molecular weight generally adjusts resorption levels versus strength of the scaffold with higher molecular weights resulting in stronger but less resorbable scaffolds and lower molecular weights resulting in weaker but more resorbable scaffolds.

Low molecular weight polymers are often capable of safely breaking down and being resorbed within the body. In general, resorbable polymers are often of very low molecular weight as compared to polymers used in common automotive, aerospace, and industrial applications. Resorbable polymers usually have as low as 2-3 orders of magnitude lower molecular weight than the polymers used in those applications.

In addition to being resorbable, ideally, the resulting implant would have sufficient "green strength" to allow post-rendering cleaning of unpolymerized material from the implant's structure including its pores. Green strength is defined as the strength of the rendered implant immediately after cDLP occurs, and after unpolymerized material is washed out, but before any post-curing such as UV light box exposure or heat-based curing.

In one embodiment, the cDLP process of the present disclosure uses the resorbable polymer poly(propylene fumarate) or PPF as the light-polymerizable material. PPF incorporates most of the characteristics discussed above for the light-polymerizable material including low molecular weight, no toxicity and resorbability. In another embodiment, the cDLP process of the present disclosure uses a resorbable light-polymerizable material other than PPF. In yet another embodiment, the cDLP process of the present disclosure uses a light-polymerizable material that although not resorbable is biocompatible or bioneutral. In one embodiment, the liquid light-polymerizable material has a molecular weight of approximately 4,000 Daltons or less. In another embodiment, the liquid light-polymerizable or light-curable material has a molecular weight of approximately 1,200 Daltons or less. In yet another embodiment, the light-curable material has a molecular weight in the range of 1,000 Daltons and 20,000 Daltons. However, other molecular weight ranges are possible, including, 1,000-5,000 Daltons, 2,500-8,000 Daltons, 7,500-15,000 Daltons, etc.

Also contemplated herein are implants and resorbable implants and biocompatible structures that are manufactured by stereolithography continuous digital light processing, or other photocrosslinking-based 3D printing methods which may or may not have pores, and may or may not have cells, growth factors and/or other constituents suspended in the hydrogel. The polymer or polymers selected can affect the ability of other constituents in the resin to bind to each other and the one or more polymers and also the other physical interactions between the polymer(s) and other resin constituents.

Viscosity

Some liquid light-polymerizable materials such as PPF are highly viscous. Referring to FIG. 1, in cDLP, for example, a missed layer may result if insufficient resin 140 is available above the basement plate 130 or if air bubbles form in that layer due to excessive viscosity of the resin 140 incorporating the liquid light-polymerizable material. Viscous resins may also require a longer pause between layers, as more time is required for the flow into void spaces left in the areas where the previous layer was cured. Longer exposure times (and/or just highly viscous material) can also lead to unwanted adherence of the scaffold to the transparent basement plate during the build process.

Use of a solvent may alleviate these issues by reducing the resin's viscosity. The addition of substances that are ultimately bound into the manufactured part, such as powders (i.e. solid crystals), ceramics, or other components may require the use of a solvent to dissolve the additives in the resin. However, the use of a solvent may affect the rigidity of the implant or scaffold, with higher amounts of solvent making the implant less rigid. Ideally the resin's viscosity would be reduced without sacrificing implant rigidity. Moreover, any substance used to reduce the resin's viscosity would have to possess some of the same characteristics described above for the liquid light-polymerizable material including little or no toxicity.

In one embodiment where the liquid light-polymerizable material used in the resin 140 is PPF, diethyl fumarate (DEF) is added to the resin 140 to reduce the resin's viscosity. DEF is a monomer precursor to PPF. This monomer cross-links into the resulting implant or scaffold and once cross-linked poses little to no toxicity risk. In one embodiment, the proportion of DEF to PPF is about 1:1 by weight. Other proportions of DEF to PPF by weight include: about 1:3 to about 1:0.5. In yet another embodiment, the substance used to reduce the resin's viscosity is a substance other than DEF. In one embodiment, no substance is added to the resin to reduce the resin's viscosity.

Other substances, e.g. diluents, may also be added to a resin composition to improve its "flow" characteristics, as some resins may not necessarily flow well at room temperature or the desired temperature of use. DEF, for example, may be used to also improve the flow characteristics of resin compositions, including PPF resins. Solvents can perform the same function as diluents under some circumstances.

Photo-Initiators

Photo-initiators are added to the resin, including to the light-polymerizable material in order to promote the polymerization reaction. Photo-initiators required for use in tissue engineering must be non-toxic and biocompatible. Photo-initiators can include bisacylphosphine oxides, for example, bis(2,4,6-trimethylbenzoyl)phenylphosphine oxide (BAPO) brand name Irgacure® 819 (BASF (Ciba Specialty Chemicals)), or Bis(.eta.5-2,4-cylcopentadien-1-yl)-bis(2,6-difluoro-3-(1H-pyrrol-1-yl)-phenyl) titanium, brand name Irgacure® 784 (BASF (Ciba Specialty Chemicals)) is used. Other Irgacure photo-initiators may also be used, e.g. Irgacure 184, Irgacure 250, Irgacure 754, Irgacure 819-DW, Irgacure 1173, Irgacure 2022, Irgacure 2100, Irgacure BP, Irgacure TPO, and Irgacure TPO-L. See *Dispersions & Pigments North America*, BASF, http://www.dispersionspigments.basf.us/p02/USWeb-Internet/pigments/en_GB/content/microsites/pigmentsdispersions/products/Irgacure.

As described in *Photoinitiated Cross-Linking of the Biodegradable Polyester Poly(propylene fumarate). Part I. Determination of Network Structure*, by Fisher et al., Biomacromolecules 2003, 4 1327-1334, bisacylphosphine oxides (e.g. BAPO) are one of three basic members of the acylphosphine oxide class of photo-initiators. Other members of the class are monoacylphosphine oxides (MAPO) and trisacylphosphine oxides (TAPO). All of these compounds undergo cleavage of the benzoyl-phosphinoyl bond upon irradiation, producing free radicals. Other compounds such as phenylglyoxylates, hydroxyketones, alpha amino ketones, alpha hydroxyl ketones, benzildimethyl ketal, sulfonium salts, oxime esters, photoacid generators and combinations of any of the foregoing, can also be used as photo-initiators herein.

Still other agents can be used as photo-initiators, for example benzophenones (e.g. oxybenzone (2-Hydroxy-4-methoxybenzophenone)), camphorquinone, and other photo-initiators that produce free radicals in the presence of the light selected for the additive manufacturing process. Photo-initiators such as oxybenzone, camphorquinone and others may require a co-initiator in order to produce free radicals that aid in the curing process. The co-initiator may be dimethylamino benzoic acid ethylester ("DMABE") or triethanolamine ("TEA") or any other agent that aids in the photo-initiator's production of free radicals. The wavelength of light used in the manufacturing process, the type of free radicals produced by the photo-initiator and their rate of formation will determine an initiator's effectiveness at producing crosslinks necessary to cure the resin.

In one embodiment, the percentage by weight of initiator in a resin including a liquid light-polymerizable material is in the range of about 0.5%-1.0% (w/w) relative to the weight of the liquid light-polymerizable polymer(s) and any solvents used. Other ranges include, about 0.75%-1.5% (w/w), about 1.0-2.0% (w/w), about 2.0-3.0% (w/w). Ranges less than about 0.5% and greater than about 3.0% (w/w) are also contemplated.

Dye

As discussed above, the between-plane (z) resolution of the cDLP process may be further controlled by controlling the depth of penetration of polymerizing light energy into the light-polymerizable material being cured or previously cured implant layers. Some level of light penetration into previously rendered layers may be desired to ensure overcuring or stitching between layers, also known as interlayer binding. However, if light penetrates too deeply, previously cured layers may overcure resulting in undesired characteristics of the resulting implant or scaffold.

A dye or pigment (referred to herein generally as "dye") is added to the resin including to the light-polymerizable material to, at least in part, control the depth of penetration of polymerizing light energy into the scaffold or implant layers and therefore, assist in controlling interlayer binding. The dye may possess several of the same characteristics described above for the light-polymerizable material including no toxicity. For example, dyes such as azo-chromium dye that may provide adequate control of the depth of penetration of polymerizing light energy into the scaffold or implant layers are toxic and thus, may not be well suited for implant applications. A property of the chosen dye to take into consideration is its ability to stay suspended in a liquid light-polymerizable resin throughout the rendering process. For some dyes, it may be necessary to stop the process and re-stir the resin if the dye is settling out. Viscosity, temperature and motion may affect the ability to dissolve the dye or other resin constituent.

Since the dye used in a dye-initiator package is likely to be incorporated into the scaffold, it may be useful to use dyes that could also positively influence scaffold surface roughness, act as a bioactive compound such as an antibiotic, or otherwise affect the scaffold degradation environment (e.g., buffer the pH if it would otherwise be too acidic or basic). In one embodiment, a dye used is doxycycline hyclate. In another embodiment, a dye used is amphotericin B. Dyes such as titanium dioxide ($TiO_2$) can be added to the resin including to the light-polymerizable material to partially control the depth of penetration of polymerizing light energy into the scaffold or implant layers. Dyes other than $TiO_2$ or a combination of dyes which include dyes other than $TiO_2$ can be added to the resin including the liquid light-polymerizable material to control the depth of penetration of polymerizing light energy into the scaffold or implant layers.

Referring back to FIG. 1, in one embodiment, the DMD projector 110 projects light 120 upward through the basement plate 130 above which is a resin 140 that includes a dye. The dye limits the depth of penetration of the light 120, thereby improving control of the curing depth of each individual voxel. The concentration of dye used can be varied to control the depth of penetration of light 120. The amount of dye present in the resin 140 affects the amount of energy that is imparted to the polymerization reaction.

The dye limits the depth of polymerization allowing for the option of using higher levels of irradiance without losing resolution in the z direction. The current layer may be cured at a high energy level without excessive overcuring of previously rendered layers. The use of higher levels of light energy in this way may increase implant green strength.

In one embodiment, the dye concentration in the resin is between about 1-5% by weight of the polymer(s) and any solvent used (% w/w) to reduce the depth of penetration of light to approximately 120 micrometers with 50 micrometer layers and 70 micrometers of overcuring to previously rendered layers. In another embodiment, the dye concentration in the resin is between about 0.01 and about 0.2% by weight of polymer(s) and any solvent(s) in the resin, although other ranges are possible, e.g., between about 0.2 and 0.5% by weight of polymer(s) and any solvent(s) in the resin, lower than about 0.2% or higher than about 5% by weight. Over-curing of previous layers may be selected to be in the range of between about 10% and 300%.

Dye-Initiator Package

Figure 2:
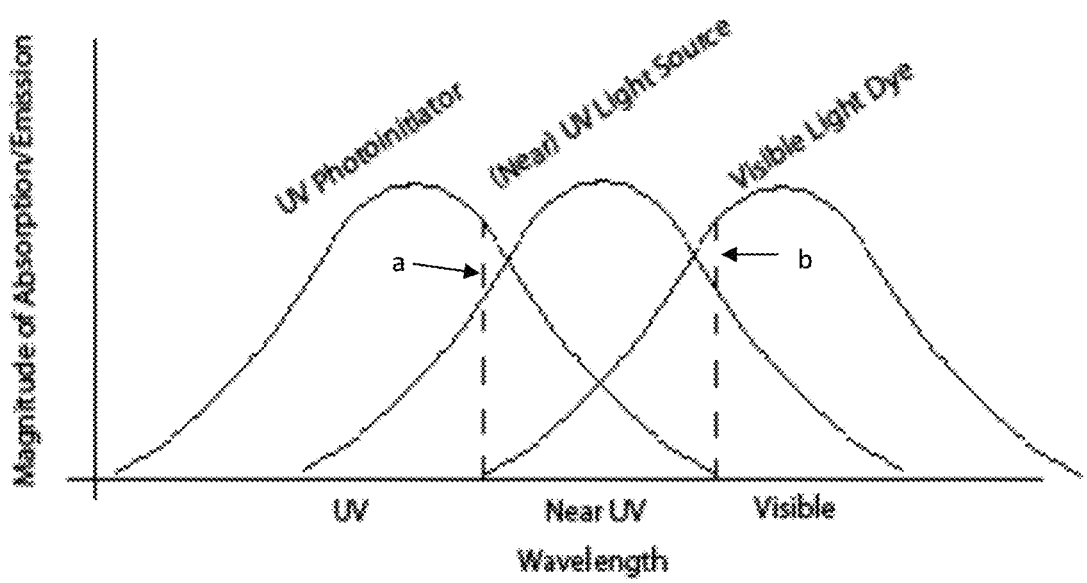
FIG. 2 illustrates an exemplary chart plotting wavelength versus magnitude of light absorption/emission for an initiator, a light source, and a dye.

FIG. 2 illustrates an exemplary chart plotting wavelength versus magnitude of light absorption/emission for the initiator, the light source, and the dye. The primary function of the dye is to block light. For many dyes, this will be accomplished by light absorption. For other dyes, this is accomplished by light reflection or scattering. Thus the dye will compete with the initiator for photons. The area between the lines a and b in FIG. 2 is the area where the cDLP process has the greatest control over depth of light penetration and amount of polymerizing energy imparted to the initiator. Light of a wavelength to the left of line would not be blocked by the dye, whereas, light of a wavelength to the right of line b would not cause proper polymerization of the resin.

To further reduce the depth of penetration of light, the amount of dye in the resin may be increased. However, it may also be necessary to increase the amount of initiator present as the amount of dye is increased. Thus, the dye and initiator form a "dye-initiator package" because the amount of each included in the resin would depend upon the amount of the other. Further, the selection of one or more dyes/ initiators in the resin will vary depending on the wavelength of light used in the 3D printing process. The chart of FIG. 2 is exemplary and other wavelengths of initiator, light source, or dye could be used resulting in a different chart.

Overall strength of the scaffold or implant once it is fabricated is a function of cross-linking density, which may be affected by the components in the resin, e.g. one or more dyes and/or initiators. For example, use of more initiator will produce stronger parts (scaffold, implant, etc.), however, without increasing the amount of dye, the layer polymerized will be thicker and resolution in the "z" direction will decrease. In some instances, the components and quantities may be tuned so that they work together. For example, when used with $TiO_2$, Irgacure 784 allows the use of less $TiO_2$ in the resin composition, and has beneficial photoinitiating properties. Increasing the amount of energy in the correct wavelength of light will also produce more crosslinks. However, this too will increase layer thickness thereby reducing between layer resolution. Increasing the relative amount of polymer in the resin will also allow for the production of more crosslinks, however, increasing the amount of polymer requires increasing the amount of initiator to crosslink the polymer, which will increase layer thickness. The components selected for the resin must be selected based on the wavelength of light used in the manufacturing process. Dyes are chosen that limit light of wavelengths that best activate the initiator from penetrating the resin, however, the limitation of light penetration should not be so great that the initiator cannot function. In some cases it may be possible to tune the resin so that no dye is needed because the constituents selected allow for curing the desired layer thickness without the need to control the light penetration.

A dye-initiator package that is essentially one or more photo-initiators (a "photo-initiator" package), tuned to cure the light polymerizable polymer(s) at a desired layer thickness and resolution but without the use of a dye may include a first photo-initiator and a second photo-initiator wherein the first photo-initiator cures the composition when exposed to a first light source in an additive manufacturing device and the second photo-initiator limits the transmission of light that activates the first photo-initiator in the additive manufacturing device. One or both of the photo-initiators may be an acylphosphine oxide, an alpha hydroxyl ketone, a phenylgloyoxylate, a benzophenone, or a combination of any of the foregoing, selected based on their activation potentials at the wavelengths of light used by the additive manufacturing device, and their capacity to initiate photopolymerization of the polymers used in the additive manufacturing process. When used for additive manufacturing of resorbable, biocompatible scaffolds or implants, the first photo-initiator may be BAPO and the second photo-initiator may be Bis(.eta.5-2,4-cyclopentadien-1-yl)-bis(2,6-difluoro-3-(1H-pyrrol-1-yl)-phenyl) titanium. The first and second photo-initiators may each be provided in amounts of about 0.1 to about 5.0% by weight of the polymer(s) and any solvent(s) used in the composition.

Light Absorber

The dye-initiator package may also include a light absorbing agent. While $TiO_2$ is biocompatible, stable, and small in particle size, making it ideal for use in photo-initiated polymer mixtures, it has strong light scattering properties, which leads to inadvertent curing, called "dark cure", resulting in decreased within layer resolution, or "x-y" resolution. Light scattering also causes too much curing in the "z" direction, which can cause curing of material in place of the pores in the scaffold or other unwanted polymer curing between the implant layers. One way to adjust for light scattering and control the within-layer ('x-y') resolution of the 3D printing process is the use of a light absorber. A substance that absorbs light, reducing or preventing light penetration beyond a known depth may be added to the resin. According to one embodiment, the light absorber used is oxybenzone (2-Hydroxy-4-methoxybenzophenone), also known as "HMB" (Sigma-Aldrich, CAS No. 131-57-7), which is an ultraviolet light absorber and has the following structure:

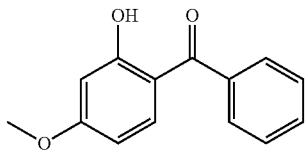 [SMILES: COc1ccc(C(=O)c2ccccc2)c(O)c1]

The ability of oxybenzone to absorb UV light is due to molecular interactions, including the overlapping of pi bonds of both phenyl rings and that of the C=O group, that creates a completely conjugated molecule. The partial integration of the C=O group and the two phenyl rings stabilizes the system due to the transference of electron deficiency from the carbon of the carbonyl toward the carbons in the phenyl rings. Castro, G. T.; Blanco, S. E.; Giordano, O. S., UV Spectral Properties of Benzophenone. Influence of Solvents and Substituents, *Molecules* 5 (3): 424 (2000).

Other organic compounds with similar light absorbing capacity, such as other compounds used in sunscreens that are biocompatible may also be used. Other US FDA or other agency approved sunscreen agents include: avobenzone, bisdisulizole disodium, diethylamino hydroxybenzoyl hexyl benzoate, ecamsule, methyl anthranilate, 4-aminobenzoic acid, cinoxate, ethylhexyl triazone, homosalate, 4-methylbenzylidene camphor, octyl methoxycinnamate, octyl salicylate, padimate O, phenylbenzimidazole sulfonic acid, polysilicone-15, trolamine salicylate, bemotrizinol, benzophenones 1-12 (2,4-dihydroxybenzophenone, 2,2',4,4'-tetrahydroxybenzophenone, sulisobenzone, sulixobenzone sodium, 2,2'-dihydroxy-4,4'-dimethyoxybenzophenone, 5-chloro-2-hydroxybenzophenone, dioxybenzone, sodium 2,2'-dihydroxy-4,4'-dimethoxybenzophenone-5,5'-disulfonate, mexenone (2-hydroxy-4-methoxy-4'-methyl-benzophenone), benzophenone-2, benzophenone-6, octabenzone), drometrizole trisiloxane, iscotrizinol, octocrylene, bisoctrizole, zinc oxide.

Combining BAPO and Irgacure 784 in a resin composition for some manufacturing applications can reduce the amount of light absorber required.

The absorption spectrum of the light absorber is selected so that it absorbs wavelengths of light used in the curing process ("build phase" of an additive manufacturing process). The light absorber's absorption capacity should be such that it does not inhibit the production of free radicals by the photo-initiator but should be great enough to absorb light scattered by one or more dyes or other light attenuators used in the process, thus maintaining resolution in the xy plane. The light absorber may be a substance that acts as both a dye and an initiator, in that it prevents a desired amount of light penetration but it also produces free radicals in response to light that brings about the desired polymerization.

The percentage by weight of light absorber in a resin to weight of the liquid light-polymerizable polymer(s) and any solvents can vary from about: (i) 0.1 to 50%; (ii) 20-35%; (iii) 10%-30%; (iv) 0.1-10%.

A resin composition that includes a light absorber for the manufacturing of resorbable scaffolds and implants comprises a light-polymerizable material, about 0.1 to 5.0% (w/w) of a photo-initiator by weight of the polymer(s) and any solvents, about 5.0% to 35.0% (w/w) of a light absorber by weight of the polymer(s) and any solvents, and about 0.1 to 5.0% (w/w) of a dye by weight of the polymer(s) and any solvents. The composition may optionally include a second dye/photo-initiator in an amount of about 0.1 to 5.0% (w/w) by weight of the polymer(s) and any solvents. Other ranges contemplated by the invention (by weight of the constituent to the weight of the polymer(s) and any solvents) include: about 0.1 to 3.0% (w/w) of a photo-initiator, about 0.1 to 3% (w/w) of a light absorber, and about 0.1 to about 3.0% (w/w) of a dye. In one embodiment the composition comprises, (by weight of the constituent to the weight of the polymer(s) and any solvents): about 1.0 to 2.0% BAPO, about 8.0 to 15.0% or about 8.0 to about 30.0% oxybenzone, about 1.0 to 5.0% $TiO_2$, and about 1.0 to 5.0% Irgacure 784. In another embodiment, the composition comprises (by weight of the constituent to the weight of the polymer(s) and any solvents) about 1.0 to 3.0% BAPO, about 0.1 to 1.0% Irgacure 784, and about 0.1 to 1.0% oxybenzone.

When used as part of a photo-initiator package, the amount of light absorber required in the resin composition may be less than in other dye-initiator packages. In some cases, one of the photo-initiators may also act partially as a dye, limiting some of the light that activates the other photo-initiator. In addition, the photo-initiator may not scatter as much light as other dyes. Thus, the amount of light absorber required may be significantly lower than in other resin compositions using a dye-initiator package, and dependent on the effects of the other constituents on the light used in the additive manufacturing process. For example, when used in a photo-initiator package comprising about 0.1 to 5%

(by weight of the constituent to the weight of the polymer(s) and any solvents) of each of BAPO and Bis(.eta.5-2,4-cyclopentadien-1-yl)-bis(2,6-difluoro-3-(1H-pyrrol-1-yl)-phenyl) titanium (Irgacure® 784), oxybenzone may be added in an amount of about 0.1 to about 5% by weight of the constituent to the weight of the polymer(s) and any solvents.

According to another embodiment of the invention, a method of optimizing the constituency of a resin composition for producing a biocompatible, resorbable, tissue engineering scaffold or implant as contemplated herein includes identifying a substance that is suitable for the produce, e.g. biocompatible, and modeling the cure depth obtainable using that substance at varying concentrations over time. Identifying the substance with the strongest capacity for limiting the depth of light penetration in the resin, reduces the amount of time required to test numerous compositions for cure depth, and streamlines the process for identifying a suitable composition to make biocompatible implants. The steps of the method may include: (1) selecting a substance that exhibits the greatest capacity for limiting the transmission of light that activates a photo-initiator; (2) creating test mixtures by adding the light limiting substance to a light-polymerizable polymer at varying concentrations of the substance by weight of the polymer; (3) polymerizing the test mixtures using an additive manufacturing apparatus; (4) plotting the cure depth of the polymerized test mixtures versus the natural log of time; (5) selecting a cure depth and corresponding concentration of the light limiting substance; and (6) selecting one or more agents for a final light polymerizable composition for building the implant using the polymer and selected concentration of the light limiting substance. The light limiting substance should be selected such that it does not inhibit the functionality of the photo-initiator. Further, one of the one or more agents selected for the final light polymerizable composition may be an agent that absorbs light that is scattered by the light limiting substance in the xy plane. The method may also include modeling the effects of the one or more additional constituents to effectuate the desired properties of the final 3D printed scaffold or implant, including but not limited to qualitative, biological, functional, and chemical properties. The method may be used to determine the desired concentrations of the constituents of a resin composition as described above.

Figure 3:
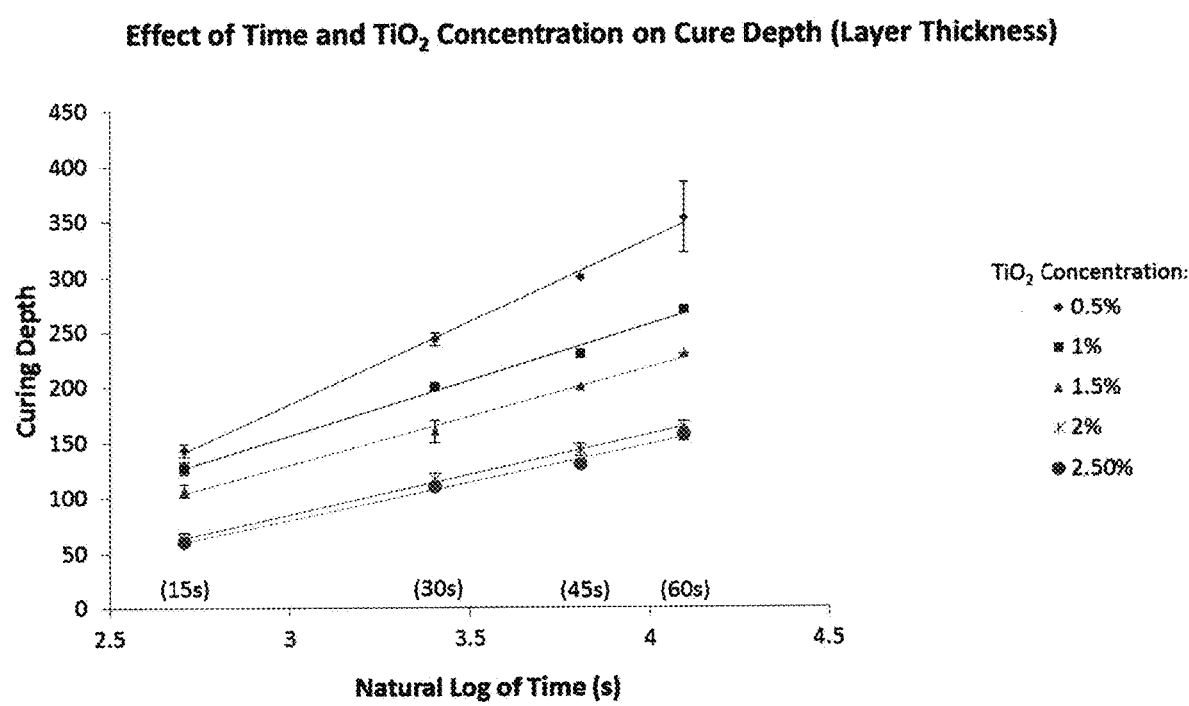
FIG. 3 illustrates a plot showing the effect of titanium dioxide dye concentration on cure depth of a layer of a liquid light-polymerizable resin.

An example of a plot of the natural log of time versus cure depth at varying $TiO_2$ concentrations in a test polymer mixture is shown in FIG. 3. This method may be used to plot, and determine, additive manufacturing resin composition based on the concentration of the strongest light attenuating substance, typically a dye or pigment.

Scaffolds

A scaffold design may include an external shape that accurately fits a patient-specific defect site. Moreover, the design may require complex three-dimensional structures.

Figure 4:
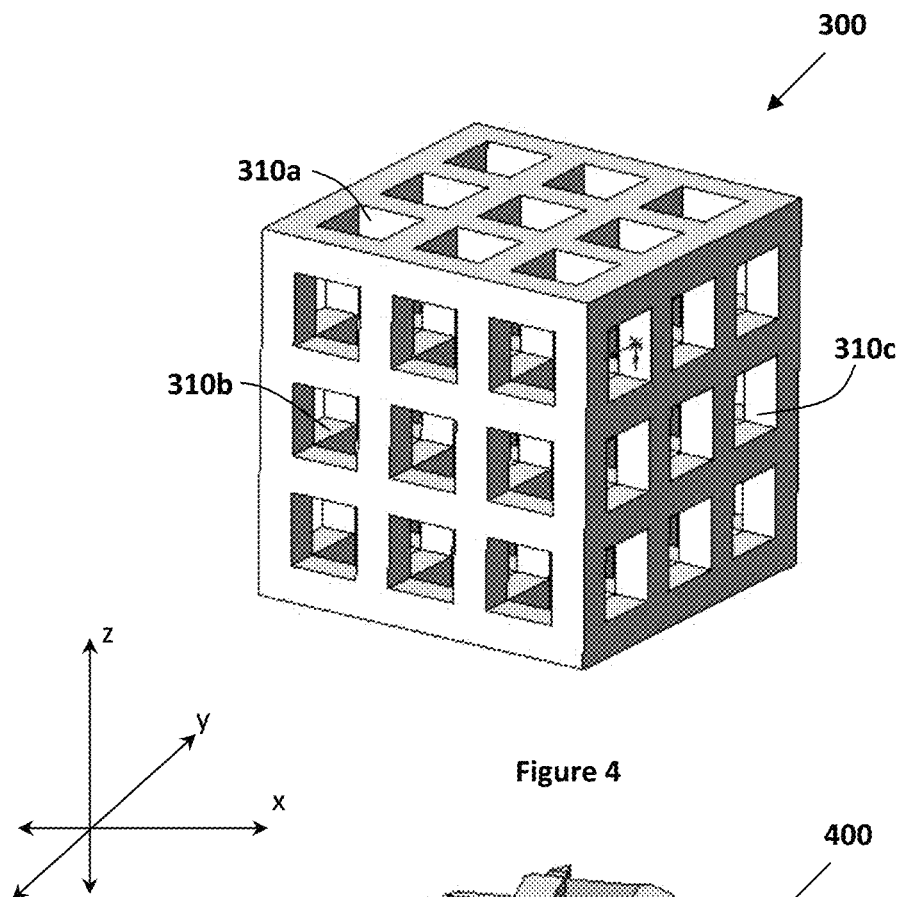
FIG. 4 illustrates an exemplary porous structure scaffold.

FIG. 4 illustrates an exemplary scaffold 300. The scaffold 300 includes pores 310a-c that are orthogonal or at right angles with the layers of the scaffold 300. The three dimensional geometry of scaffolds including internal spaces may be important to the loading of cells and the establishment of vascular channels. In one embodiment, a scaffold includes pores or internal channels. In one embodiment, the diameter of pores and channels in the scaffold is between about 150 micrometers and about 1 millimeter. In another embodiment, the diameter of pores and channels in the scaffold is between about 50 micrometers and about 1.6 millimeters. In other embodiments, the diameter of pores and channels in the scaffold is smaller than about 50 micrometers or larger than about 1.6 millimeters. Modeling of scaffold pores at these ranges may require compensation in the CAD to correct for, among other factors, post-curing shrinkage of implants or swelling due to wetting caused by pre-implantation cell culturing or implantation itself.

In addition to the scaffold design parameters relating to pore size, the design may require complex porous structures that facilitate cell loading, neotissue growth, and host tissue ingrowth. For example, the design may require that pores or channels open toward the host tissue in the defect site to allow tissue ingrowth prior to the implant's full degradation. More accurate rendering makes it more likely that complex internal pore structures can be created.

Figure 5:
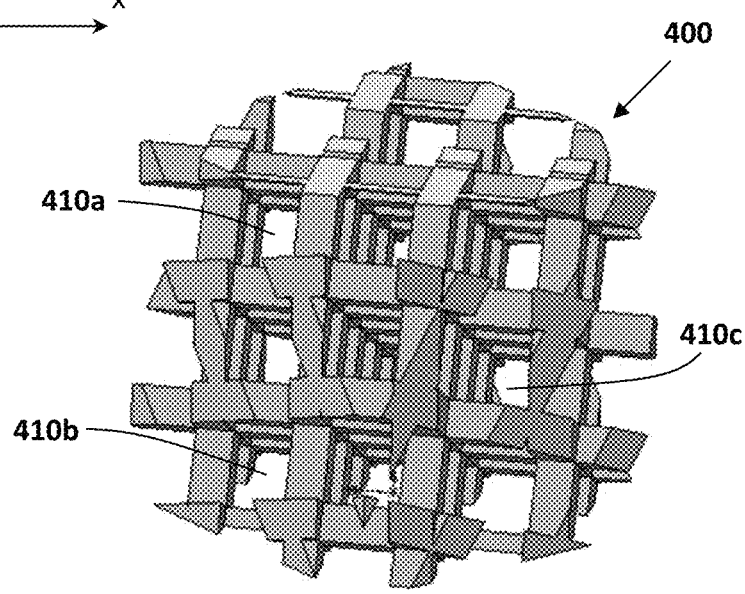
FIG. 5 illustrates an exemplary porous structure including pores that are oblique.

FIG. 5 illustrates an exemplary porous structure scaffold 400. The scaffold 400 includes pores 410a-c that are oblique. Oblique is defined to be any direction that is not parallel to the x, y, and z directions by which scaffolds are rendered using the above described additive manufacturing techniques. Oblique construction (non-orthogonal) may be important with respect to external surface as well as pore structure to make sure that the host's tissues do not encounter a wall (barrier) in the scaffold, which is more likely when pore structures are built orthogonally than when pores and/or channels are oriented towards the host tissue. The implant designer may want to orient pores and/or channels within a scaffold so that they open toward the host's tissue thereby facilitating growth of new tissue into the implant and active incorporation of the implant into the host's tissues.

Additive manufacturing devices with voxel resolution in the range of 100-1000 micrometers may be able to bring about orthogonally oriented pore structures, however they may provide insufficient resolution to produce obliquely oriented pores in these ranges. Resolution of the cDLP device is such that rendering of structures having obliquely oriented pores is possible.

Additionally, in tissue engineering scaffold applications where an initial goal is cell attachment, PPF's hydrophobic surface can be modified through radiofrequency glow-discharge (RFGD) or by soaking the implant in serum to provide for protein adsorption. Cell attachment can also be mediated by other factors embedded in the surface that mimic extracellular matrix components. This includes surface roughness, which may include indentations and protrusions having diameters ranging from 1 nanometer to 100 micrometers, as well as the material's compliance.

Once attached, the goal is likely to shift to cell proliferation and eventually maturation as host tissue integrates. In addition to the effect the dye has on surface roughness, other compounds, such as tricalcium phosphate crystals, can be added to the resin in the additive manufacturing device. However, as with the dye, depending on solubility, crystal size, and tendency to aggregate, it may be difficult to keep these crystals suspended in the resin at a relatively constant concentration throughout the scaffold rendering process. The crystalline structure, and size of any of the constituents used in the resin composition can vary and be used to change the features of the resulting scaffold.

Scaffold design features, such as wall thickness, affect the macro strain distribution and may be optimized to resist trauma. Moreover, it may be necessary to counterbalance desired resorption processes with the need for the implant to be loaded during tissue regeneration. The need to localize strain-bearing portions of a scaffold may necessitate the consideration of regions lacking porosity or regions rendered with composite materials, some of which may not degrade.

Post Rendering/Post Curing

Final part accuracy may be dependent upon thorough part cleaning/post rendering. This may be necessary to remove any residual uncured resin which would crosslink post rendering. The choice of washing procedures in turn relies on the mechanical integrity of the resin as cured by the cDLP process or green strength. Parts which are accurately rendered but remain soft may become damaged by improper handling or the use of harsh solvents. Once cleaned, final part strength may be improved by post-curing in a UV bath. Parts to be used in medical procedures, e.g. implants to be implanted into patients, will be handled in surgical suites and thus require sufficient strength for the necessary cleaning, sterilization, and handling as part of the pre-surgery process.

Post-curing can be used to tune the strength of the printed implant. In fact, a photo-initiator may be selected that is not activated at the wavelength of light selected for the build phase of the additive manufacturing process. It can be used as a dye during the build phase and as a photo-initiator during the post-curing phase (by selecting the proper wavelength to activate it during post-curing), to increase crosslinking density of the implant. Other ways to use a photo-initiator during the post-curing phase without activating it during the build phase include limiting the light used during the 3D printing phase, or block enough of the light during the printing phase that the photo-initiator is not activated until post-curing.

Figure 6:
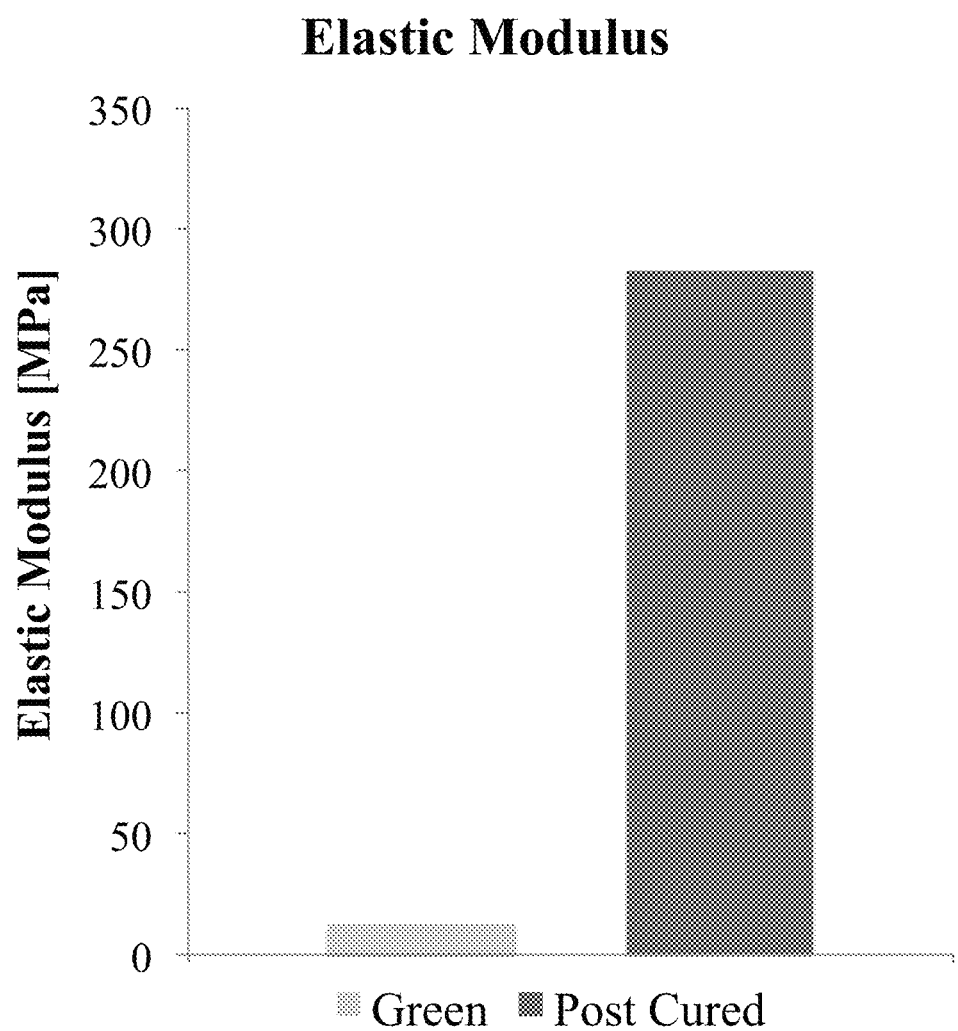
FIG. 6 illustrates the elasticity of a post-cured 3D printed scaffold compared to a "green" (non-post-cured) scaffold.
Figure 7:
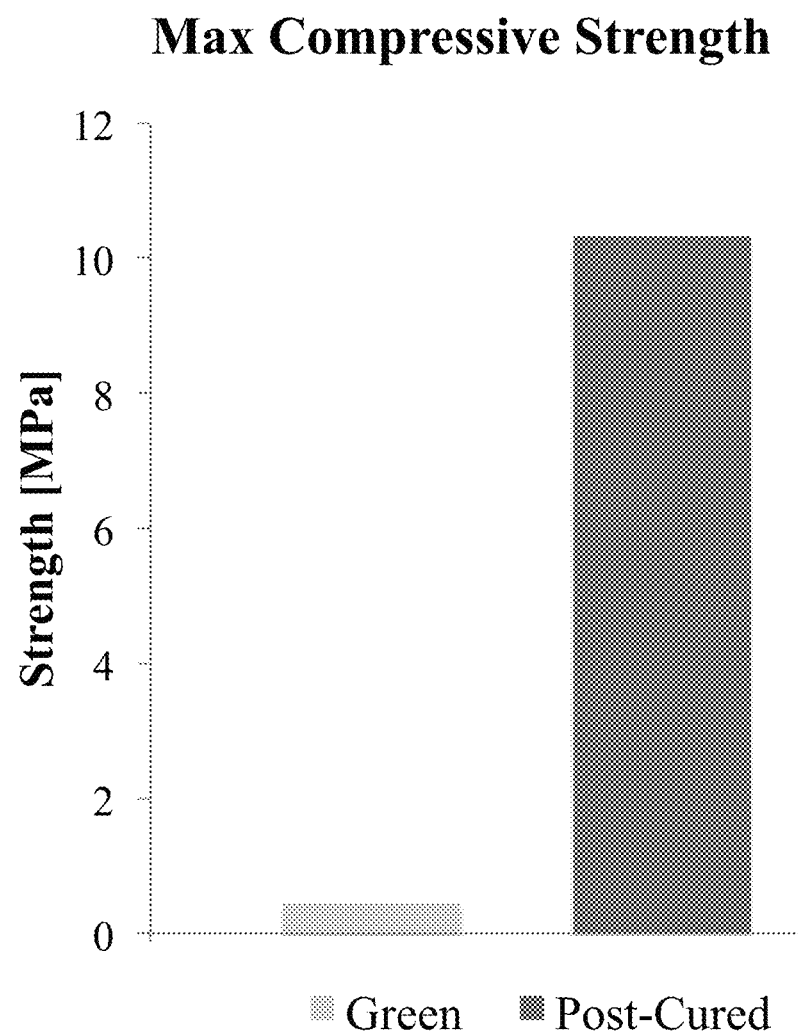
FIG. 7 illustrates the strength of a post-cured 3D printed scaffold compared to a "green" (non-post-cured) scaffold.

One example of a photo-initiator that may be used in this fashion, as a dye during the build phase and a photo-initiator during the post-cure phase is Irgacure 784. When used in combination with Irgacure 819 (BAPO), the BAPO is the primary photo-initiator in the build phase, and the Irgacure 784 acts as a dye (it changes the color of the resin). The Irgacure 784 is then activated during the post-cure phase. In this embodiment, a light absorber is not required as the Irgacure 784 partially limits some of the light that activates the BAPO but does not scatter the light within the resin composition during the build phase, so that xy resolution is not compromised. Further, the Irgacure 784 is not fully activated during the build phase, but is later activated during post-manufacturing, e.g. post-curing, processing of the manufactured product. The strength of cylinders built with BAPO and Irgacure 784 are shown in FIGS. 6 and 7, both as "green" cylinders (no post-cure) and after post-curing up to 8 hours in a UV light bath. The elasticity and compressive strength of the cylinders increased dramatically with post-curing.

During the build phase of any additive manufacturing process, a mixture of polymer(s) and photo-initiator(s) is exposed to localized light to cure the polymer, and after any post rendering steps (e.g. cleaning the resulting part), the part is exposed to a light bath to post-cure the polymer to a desired strength. Post-curing may be placing the part in a UV light bath for greater than 30 minutes. Post curing may require up to, or greater than, 8 hours in a light bath. Alternatively, post curing may require less than 30 minutes. Thus, post-curing time may be calibrated, using not only time but also constituency and concentrations in the resin to produce an implant with the desired mechanical properties.

Optionally, the composition used to build the part also includes one or more other agents, such as a dye, a light absorber or other agent as required by the desired end product. According to one embodiment, a light polymerizable composition comprises a light polymerizable polymer, a solvent or diluent and one or more photo-initiators.

The following example are intended to be non-limiting examples to various embodiments of the present invention.

Example 1

A first embodiment focused on the calibration of the cDLP additive manufacturing system to accurately render scaffolds with predictable properties of resorption, cell attachment and proliferation, host incorporation, and tissue regeneration.

Figure 8:
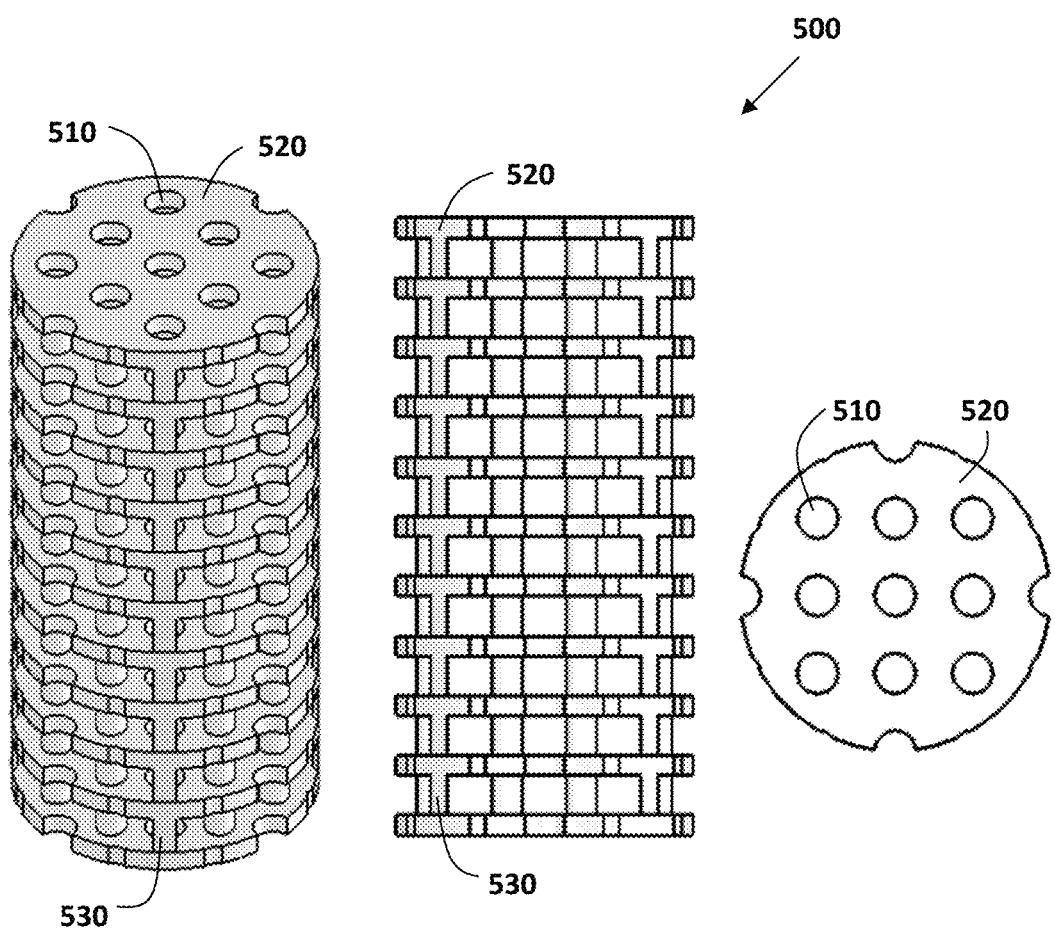
FIG. 8 illustrates isometric, front, and top views of an exemplary scaffold.

FIG. 8 illustrates isometric, front, and top views, respectively, of an exemplary scaffold 500. The goal of the calibration study was to calibrate the cDLP system for the additive manufacturing of scaffolds with the "plate and post" geometry of scaffold 500. In the embodiment, the cylindrical test scaffold was 6.0 millimeters in diameter and 12.4 millimeters in length. The diameter of the vertical channels 510 was 800 micrometers. The plates 520 were 400 micrometers thick and 800 micrometers apart from each other. The posts 530 between the plates, were 600 micrometers in diameter. The calibration of the cDLP process consisted of at least six steps.

The first step in the calibration procedure was to polymerize single layers of the cDLP resin including PPF, DEF, BAPO, and the dye. There are at least three variables to study: dye concentration, initiator concentration, and irradiance duration. Other factors that could be varied would be polymer molecular weight and polydispersity as well as irradiance level (i.e., the amount and rate at which light is applied). The goal was to have a layer thickness that insures adequate over-curing between layers, yet is thin enough to allow for a desired "z" step size and the generation of accurate geometries. Resolution in x, y, and z will determine the accuracy of the desired external and internal pore surface geometry.

The second step was to ensure that the material properties of the chosen resin configuration will provide useful scaffolds. In some cases scaffolds will be loaded with cells and/or growth factors and immediately implanted. In other cases scaffolds will be pre-cultured (e.g., in a bioreactor) prior to implantation.

The third step involved the use of the resin to form a "burn-in" patch on the basement plate on the upper elevator of the cDLP device. For this embodiment, we were not able to directly cure a burn-in patch on the build plate. Therefore, the burn-in patch was obtained by over-curing resin on the basement plate. The over-cured resin patch was then transferred to the build plate and cured onto that plate using a UV bath (Procure™ 350, 3D Systems) followed by warming with a heat gun. Heat was used to ensure that the patch center cured to the underlying build platform as the dye content of the resin could prevent UV penetration at the patch edges. Care was taken to allow the heated layer and platform to cool to prevent accelerated curing when the patch was reintroduced to the device. This procedure allowed scaffolds to cure to the PPF resin directly, rather than the metal platform itself.

The fourth step involved the transfer of the scaffold CAD file to the cDLP device for rendering. The CAD file may contain support structures spanning the space between the scaffold and the burn-in patch. The support structures rise sufficiently above the burn-in patch to allow resin to circulate between the burn-in patch and the scaffold during rendering of the scaffold and to allow washing out of unpolymerized resin following that procedure.

The fifth step involved rendering the multi-layer scaffold as discussed above.

The sixth step involved testing the scaffolds both in vitro and in vivo. In vitro testing includes mechanical tests, biological environments without cells or tissues, and biological environments with cells, growth factors, and/or tissues.

A 1200 Daltons PPF was prepared, synthesized and purified per known methods.

Briefly, DEF (Acros, Pittsburgh, PA) and propylene glycol (Acros) were reacted in a 1:3 molar ratio with hydroquinone and zinc chloride as a crosslinking inhibitor and a catalyst, respectively. This reaction created the intermediate, bis(hydroxypropyl) and ethanol as a byproduct. The intermediate was then transesterified under a vacuum to produce poly(propylene fumarate) and propylene glycol as a byproduct. The PPF was then purified and gel permeation chromatography was used to calculate the number average molecular weight (Mn=1200 Da).

R320 titanium dioxide $TiO_2$ (Sachtleben White Plains, NY) which is a 320 nanometer crystal was used. A 133 micrometer layer of PPF 4.8% $TiO_2$ (range tested: 0-4.8%), 2% BAPO (range tested 0.5-2%), 33% DEF (range tested: 33 and 50%), and an irradiance level of 200 mW/dm$^2$ for 300 seconds (60 s and 300 s were tested). A lateral spreading (i.e., in x and y) of polymerization beyond the intended layer boundaries was observed. This area increased most quickly at higher concentrations of $TiO_2$, especially with increased light input at those high dye concentrations. The area of lateral spreading was not as thickly or as strongly cured as the expected area of exposure. In order to quantify this phenomenon, an extra step was added to the normal curing test calibration procedure. In addition to measuring cured layer thickness, i.e. the z dimension, x-y dimensions were also measured.

The curing test procedure used a small square-shaped test pattern of UV exposure. At each $TiO_2$ concentration increment, the length and width of the cured square-shaped thin layer were recorded. Additionally, the length and width of the total cured area, including those areas affected by lateral polymerization, were also measured. With this data, it was possible to calculate the percent over-cure. The length and width, or x and y, measurements were averaged for each part, and this process was repeated three times (n=3) for each $TiO_2$ and BAPO concentration.

The first attempt yielded an incomplete build and a membrane of polymerized material that formed on the basement plate. This was corrected by: (1) regularly straining out polymerized resin, (2) regularly cleaning the basement plate, and (3) monitoring the basement plate throughout the 16 hour build cycle. Cleaning unpolymerized polymer from the internal pore space of the scaffolds was a simple procedure using an ultrasonic alcohol bath. The scaffolds rendered were accurate to within 80 micrometer.

Depth of polymerization (micrometers) was characterized as a function of titanium dioxide concentration (wt %) for five different combinations of BAPO concentration (wt %) and exposure time (s). From these tests, it was determined that a 2 wt % titanium dioxide concentration with 2 wt % BAPO and a 60 s exposure time would yield an average depth of polymerization equal to 133.3 micrometers. These settings could therefore be used to build in 50 micrometer layers with 83.3 micrometers of over-curing. A 200 mW/dm$^2$ irradiance was used.

High refractory index of the $TiO_2$ caused light scattering. While this scattering is in all directions rather than only in the z direction, the amount of solid layer curing continued to occur only in the z direction. There was no interlayer over-curing in other directions as there were no additional layers to the sides and the layers above the current location were not yet in existence. Increasing $TiO_2$ concentration led to an increased amount of lateral over-curing. Testing was performed using a 200 mW/dm$^2$ irradiance and a 300 s exposure time. Two levels of BAPO were tested for each titanium dioxide concentration.

The cDLP devices used can provide native accuracies of up to 13 micrometers in z and 71 micrometers in x and y, and up to 35.5 micrometers when using anti-aliasing or pixel shifting software. This is sufficient resolution to prepare patient specific implants. This resolution is high enough that surface features (e.g., surface roughness) could be rendered to ideal scales for cells to respond to.

Using 1200 Daltons PPF, we were able to use a cDLP device to render layers as thin as 60 micrometers. The resulting highly accurate scaffolds are likely to allow improvements in the modeling, prediction, and eventual design of scaffold-specific cell attachment, proliferation, maturation, and resorption parameters. The use of dye-initiator packages allow the production of very highly accurate features with sufficient green strength to allow aggressive postrendering removal of unpolymerized resin and handling.

Example 2

This embodiment was implemented on the Perfactory® UV device having a 60 millimeter lens. A relatively small amount of dye was necessary (for example, 0.01 to 0.2 wt %) of overall resin mass. The dye used in this study was at a greater concentration than is typically used in industrial applications, up to 0.5% of overall polymer mass. It is important that the dye be biocompatible. In this study, a yellow chromium azo dye was used. The amount of initiator used in this study was 2% of Irgacure® 819 (BASF (Ciba), Florham Park, NJ). The substance used in this study to reduce the viscosity of the resin was diethyl fumarate (DEF), the monomer precursor of PPF.

The designed (i.e., in CAD software) plate thickness and post diameter were 0.4 millimeters and 0.6 millimeters, respectively. The ten-plate scaffolds generated had an average plate thickness of 0.43±0.02 millimeters, and average post thickness of 0.63±0.01 millimeters. The precision of the features (i.e., low standard deviation) may be as important as the high accuracy. These features measured slightly above their designed dimensions. Although the features here were slightly larger than anticipated, there is typically a shrinkage effect which is observed in the curing of photopolymers which results in features which are smaller than as designed. This effect can be resolved in the cDLP system by manipulating the energy distribution for the voxel and the strategy used in the exposure of a single voxel data set. In designing part supports, it is critical to use a support geometry that can distort to prevent anisotropic shrinkage of the scaffold. If the part is firmly attached to the build platform, the base is unable to shrink while the rest of the scaffold shrinks, leading to anisotropy in the amount of deformation. Because one can insure the between-plan dimensions by the physical translation of the build platform and over-curing, only the in-plane dimensions need be corrected (i.e., scaled to correct for shrinkage).

Example 3

For this embodiment, the Perfactory device used had a 60 millimeter lens providing an in-plane native resolution of 71 micrometers and 35.5 micrometers utilizing pixel-shifting. The resorptive polymer, poly(propylene fumarate) (PPF), was used. A yellow chromium azo dye was added. The initiator used in this embodiment was Irgacure® 819 (BASF (Ciba), Florham Park, NJ). The substance used to reduce the viscosity of the PPF was diethyl fumarate, the monomer precursor of PPF. The between plane energy settings were calibrated to achieve a voxel height of 120 micrometers when using a 200 mW/dm$^2$ irradiance, and an exposure time of 120-240 s. The scaffold shape was composed in a Computer Aided Design (CAD) program and 6 scaffolds were rendered using a 120 s exposure. 2 scaffolds were later rendered using a 240 s exposure. 10 measurements of the overall diameter of each scaffold were collected using calipers. The intended scaffold diameter was 6 mm.

The scaffolds (n=6) rendered using the 120 s exposure had the following diameters: 5.83±0.03, 5.83±0.03, 5.85±0.04, 5.82±0.02, 5.83±0.02, and 5.85±0.03 mm. The scaffolds (n=2) rendered using the 240 s exposure had the following diameters: 6.03±0.03 and 6.02±0.02 mm. The 240 s exposure results, showed less shrinkage than the 120 s exposure parts.

Example 4

A Perfactory UV device was used to render porous cylindrical PPF scaffolds with a diameter of 6 millimeters and a length of either 1.2 millimeters (N=10) or 12.4 millimeters (N=8) with either 2 or 4 minute exposure using a "plate and post" geometry. The Computer Aided Design for this scaffold was rendered in 50 micrometers thick layers with a 120 micrometers curing depth to insure sufficient over-curing (inter-layer binding). A yellow chromium azo dye, Irgacure® 819 (BASF [Ciba], Florham Park, NJ) initiator, and diethyl fumarate were added to the primary material, PPF, and used for scaffold production. A 500-195-20 Mitutoyo (Aurora, IL) caliper was used to measure scaffold features. The 12.4 millimeters scaffolds were micro-CT scanned. The 1.2 millimeters scaffolds were imaged via scanning electron microscope (SEM).

Qualitative analysis of micro-CT images presented anisotropic but predictable shrinkage. Qualitative analysis of SEM images presented thinning at layer margins. The 1.2 millimeters scaffolds presented an average observed post diameter (expected 0.4 mm) of 0.43 millimeters (0.02 std dev) and an average observed plate diameter (expected 0.6 mm) of 0.63 millimeters (0.01 std dev). The 12.4 millimeters (4 min exposure group) presented an average diameter (expected 6 mm) of 6.03 millimeters (0.03 std dev). Accurate calibration of over-curing insures interlayer binding and full formation of the smallest, 400 micrometers in this study, scaffold features.

Example 5

Poly(propylene fumarate) (PPF) with an average molecular weight (Mn) of 1200 Daltons was synthesized using the two step process described above. DEF was added in a ratio of 1 g DEF/2 g PPF to lower the viscosity of the material. The photo-initiator BAPO (BASF (Ciba), Ludwigshafen, Germany) was added in a concentration of 5, 10 or 20 mg/g of combined PPF/DEF resin mass. The titanium dioxide concentrations utilized during calibration varied from 0-48 mg TiO$_2$/g of PPF/DEF. Rutile titanium dioxide with an average particle size of 300 nm (Sachtleben, Duisburg, Germany) was used. In combining the components listed here, a particular order was useful to expedite the mixing process and more quickly achieve homogeneity of the resin. BAPO was first added to DEF, which is of much lower viscosity than PPF, and was mixed until thoroughly dissolved. The PPF was then heated to lower its viscosity before adding the DEF/BAPO mixture. Care was taken to avoid excessive temperatures (>70° C.) which could cause the polymer to crosslink. Once the PPF/DEF/BAPO mixture was prepared, TiO$_2$ was added in incremental steps to allow for calibration of curing parameters as a function of T TiO$_2$ concentration.

The cDLP-based additive manufacturing device used for this study was the Perfactory® Mini Multi Lens (envisionTEC, Ferndale, MI), which was operated in UV mode. Curing tests were performed to determine the relationship between TiO$_2$ concentration and cured layer thickness. To perform each test, a few drops of resin were placed on a glass slide. The Perfactory device was used to cure the resin with a fixed irradiance and time using a square-shaped test pattern. A 200 mW/dm$^2$ irradiance was used for these tests, and care was taken to calibrate for the added thickness of the glass slide. An exposure time of either 60 or 300 s was used. After the specified time period had elapsed, the excess uncured polymer was removed from the slide leaving only the solid square test pattern. A razor blade was used to remove the thin layer from the slide, and digital calipers were used to measure the thickness of the layer. Three replicates were performed for each unique combination of BAPO and TiO$_2$ concentration evaluated.

Example 6

Resin was prepared using a 1 g DEF/2 g PPF ratio. 20 mg BAPO/g resin and 10 mg TiO$_2$/g resin were used. A successful build required proper attachment of the cured resin to the build plate as the initial layers are cured. Some difficulty was encountered in achieving attachment between the PPF resin and the build platform using industry standard methods, and some intervention was required. A thin base plate was first rendered using two 50 micrometers layers, which did not attach properly to the build platform but later remained fixed to the transparent basement. The thin plate was carefully removed from the basement using a razor blade and placed directly onto the center of the build platform outside of the Perfactory device. Care was taken to remove any air trapped between the base plate and the platform. The base plate was then cured for 20 minutes in a UV bath. In addition to UV exposure, a heat gun was used to finalize the curing of the base plate in order to achieve a strong bond to the build platform. Providing a preattached base plate generated from PPF resin provided proper attachment of the desired parts during the subsequent build. Once this step was completed, the test scaffolds were built using a 200 mW/dm$^2$ irradiance and a 150 s exposure time.

Some post-processing of the test parts was necessary. The test parts were rinsed first with acetone and then with 200 proof ethanol to remove any excess uncured resin from the internal pore spaces. Compressed air was also used to clean the test scaffolds. Once the parts were free of uncured resin, the build platform was placed in a UV bath and 2 hrs of additional exposure were applied to fully cure the resin and strengthen the parts. The base plate was then separated from the build platform, and the individual test scaffolds were removed from the base plate. The scaffold supports were removed using a razor blade.

The resin used to render the full scaffolds was thinned by adding DEF to increase the concentration to 1:1 PPF/DEF. This was necessary as the resin viscosity had increased due to autopolymerization of the material. The BAPO and $TiO_2$ concentrations were effectively reduced in this process to 15 mg BAPO/g resin and 0.75 mg $TiO_2$/g resin. A pre-attached base plate was used as described above. Scaffolds were rendered using a 200 mW/dm² irradiance and a 150 s exposure time. After the build process completed, the scaffolds were removed from the build platform and rinsed with 200 proof ethanol. Additional cleaning involved alternating steps of ethanol rinsing, the use of compressed air, and ultrasonic cleaning in ethanol. The use of acetone was avoided as it was found to damage test scaffolds. Once the excess resin had been removed from the scaffolds, they were placed in a UV bath for 2 hrs. The scaffold supports were removed using a razor blade.

Bone marrow was obtained from adult, human volunteers. Primary cultures of isolated hMSCs were seeded. The primary isolates of hMSCs were sub-cultured at a density of 250,000 per culture flask. The hMSCs were trypsinized. Cells were counted and dense cell infusate was prepared at 32.5 million cells/2 ml for seeding of scaffolds. Four PPF scaffolds were rendered, sterilized with ethylene gas oxide (140° F.), and pre-wetted by immersion in 10% fetal bovine serum for 12 hours. The number of hMSCs loaded in each scaffold was 3.25 million (the optimal cells seeding density was based on estimated cell diameter and scaffold surface area). The 200 μL of hMSC infusate was layered onto the scaffolds in a multi-well plate (low-attachment plastic) with micropipette. The plate was placed in a vacuum chamber which was rapidly pumped down to 25" Hg for 1 min. The scaffolds loaded with high density cell-infusate were then incubated for two hours to facilitate cell attachment.

At the end of two hours the wells were filled with culture medium (DMEM-LG with 10% fetal bovine serum) to prevent drying. The scaffolds were harvested sequentially at four time intervals: 6, 24, 30 and 48 hours. All the scaffolds were fixed with 1% glutaraldehyde solution for 30 minutes and then rinsed with and stored in phosphate buffered saline (PBS) at 4 degree centigrade for Scanning Electron Microscopy (SEM).

Example 7

The effect of a dye-initiator package comprising $TiO_2$, oxybenzone (as light absorber), and BAPO on the z-axis resolution of PPF scaffolds was tested by performing single layer curing tests on the Perfactory P3 (EnvisionTEC Brusseler Straße 51, D-45968 Gladbeck Germany). A test regime using a ratio of PPF:DEF of 1:1 at set levels of BAPO and HMB while the percentage of $TiO_2$ (the "curing test mixture", or "CTM") in the composition was varied. Only test #1 shown in table 1 below used a PPF:DEF ratio of 2:1.

A mask generation was performed on the Perfactory to calibrate the light intensity to 260 mW/dm2 using the built in radiometer over a glass slide (Fisher) on top of the calibration plate. The exposure-time was then set to 120 seconds. Six to seven drops of the CTM in testing were placed in the middle of the slide. After the curing-test, the slide was removed turned upside down and dabbed off on a paper-towel so that all access-uncured material was removed. The cured test-square was carefully measured. Inadvertent curing caused by scattered light was noted should it be observed. The test-square was then carefully removed using a razor blade and observations of strength were noted.

It was found that a small amount of $TiO_2$, in conjunction with oxybenzone, permits an increase in crosslinking density (compared to $TiO_2$ alone) by dispersing throughout the resin and absorbing the light "scatter" caused by the $TiO_2$, thereby helping to improve xy plane resolution (compared to $TiO_2$ alone) but also aiding in the catalyzation of the curing process. Absorbing the scattered light allows the addition of more light into the resin to locally catalyze the polymer. Oxybenzone is also much more readily suspended in PPF than $TiO_2$, which helped increase the strength of the resulting parts. Overall, the $TiO_2$/HMB/BAPO dye package allowed the manufacturing device to run unattended while maintaining, and in fact, improving the resolution of the resulting resorbable polymer implants. Table 1, below, provides the compositions tested in the cure tests. Table 1 shows the w/w % where the percent is the weight of the particular ingredient over the total weight of the polymer and solvent.

TABLE 1

| Test Number | Orig. Test Identifier | BAPO (%) (w/w) | HMB (%) (w/w) | $TiO_2$ (%) (w/w) | Layer Thickness (μm) (# trials averaged) | Exposure Time (s) | Comments/ Qualitative Assessment |
|---|---|---|---|---|---|---|---|
| 1* | 1 | 0.25 | 1 | 0 | 460 (1) | 150 | |
| 2 | 2 | 0.19 | 10 | 0 | 43 (3) | 150 | |
| 3 | 3 | 0.3 | 10 | 0 | 78 (3) | 150 | |
| 4 | 4 | 0.5 | 10 | 0 | 164 (6) | 150 | |
| 5 | 5 | 0.5 | 12 | 0 | 132 (10) | 150 | |
| 6 | 11 | 0.35 | 7 | 0 | 310 (1) | 150 | |
| 7 | 12 | 0.35 | 15 | 0 | 138 (5) | 150 | |
| 8 | 17 | 0.3 | 15 | 0 | 136 (11) | 150 | |
| 9 | 24 | 0.4 | 17 | 0 | 225 (2) | Not recorded | |
| 10 | 24 | 0.4 | 25 | 0 | 137 (2) | Not recorded | |
| 11 | 25 | 0.4 | 28 | 0 | 114 | Not recorded | |
| 12 | 28 | 1 | 33 | 0 | 118 (10) | 150 | |
| 13 | 29 | 1 | 0 | 0 | 498 (4) | 150 | |
| 14 | 29 | 1 | 10 | 0 | 380 (1) | 150 | |
| 15 | 29 | 1 | 25 | 0 | 250 (2) | 150 | |
| 16 | 30 | 1 | 25 | 1 | 190 (5) | 150 | |
| 17 | 31 | 1 | 25 | 2 | 157 (3) | 150 | |
| 18 | 32 | 1 | 25 | 3 | 135 (4) | 150 | |
| 19 | 35 | 1 | 0 | 0 | 525 (1) | 78 | |
| 20 | 36 | 1 | 0 | 1 | 273 (3) | 78 | No HMB-large dark cure zone |

TABLE 1-continued

| Test Number | Orig. Test Identifier | BAPO (%) (w/w) | HMB (%) (w/w) | TiO$_2$ (%) (w/w) | Layer Thickness (μm) (# trials averaged) | Exposure Time (s) | Comments/ Qualitative Assessment |
|---|---|---|---|---|---|---|---|
| 21 | 36/37 | 1 | 5 | 1 | 231 (5) | 78 | Dark cure zone reduced |
| 22 | 37 | 1 | 15 | 1 | 170 (1) | 78 | Dark cure zone present on some runs |
| 23 | 37 | 1 | 15 | 2 | 145 (3) | 78 | Dark cure zone barely present |
| 24 | 38 | 1 | 0 | 2 | 220 (4) | 78 | |
| 25 | 38 | 1 | 0 | 5 | 122 (2) | 78 | Reduced thickness |
| 26 | 40 | 1 | 26 | 1 | 132 (5) | 78 | No dark cure zone |
| 27 | 41 | 1 | 20 | 1 | 180 (4) | 78 | No dark cure zone |
| 28 | 43 | 1 | 28 | 1 | 140 (3) | 72 | No dark cure zone |
| 29 | 43 | 1 | 28 | 1 | 124 (11) | 65 | No dark cure zone |
| 30 | 44 | 1 | 28 | 1 | 120 (4) | 60 | No dark cure zone |
| 31 | 44 | 1 | 28 | 1 | 190 (1) | 120 | Minor dark cure |
| 32 | 45 | 1 | 28 | 1 | 120 (3) | 60 | No dark cure- used for successful build |

Table 1 shows the progression of trials in an attempt to build a successful scaffold, varying the ratio of PPF:DEF, the quantities of BAPO, HMB and TiO$_2$, and the time the mixture is exposed to UV light. Test number 1 shows that a ratio of PPF:DEF of 2:1 is too high, resulting in a layer thickness of 460 μm. (The target was 120 μm). Test numbers 2 through 5, using a ratio of PPF:DEF of 1:1 show that with no TiO$_2$, and increasing the quantity of HMB in the composition, at an exposure time of 150 seconds, at very low levels of BAPO, e.g. 0.19 to 0.5%, and 10% HMB, the layer thickness increases from an average of 43 μm to 164 μm. Maintaining 0.5% BAPO, and increasing the HMB to 12% decreases the layer thickness to 120 μm, at an exposure time of 150. The presence of scattering, or "dark cure" of the resin was not noted as the initial trials were aimed at optimizing the dye-initiator package, using BAPO, HMB and TiO$_2$. Test number 6 show that decreasing the amount of initiator, but also the amount of dye increases the layer thickness. Increasing the amount of dye in test 7 reduced the layer thickness. Tests 9 through 11 further illustrate that if the amount of initiator is increased, the amount of dye needs to increase to maintain the layer thickness within a desired range.

Tests 12 through 15 illustrate a jump in BAPO concentration to 1%, with no addition of TiO$_2$ while varying the amount of HMB from 0 to 33%. A higher amount of HMB is clearly needed to reduce the layer thickness, but the scaffolds built with a sufficient amount of HMB (33%) but no TiO$_2$ resulted in adequate resolution but insufficient strength: the parts were too weak to be handled.

A mixture of 1% BAPO, 25% HMB was chosen to begin increasing the amount of TiO2. As the TiO$_2$ concentration increased from 1 to 3% in test numbers 16-18 the layer thickness decreased from 190 to 135 μm, but the exposure time remained 150 seconds. In order to make the process more efficient, while maintaining accuracy, the concentrations of the constituents were again varied, next by decreasing the exposure time.

Tests 20-23 illustrate the need for HMB to eliminate the dark cure, or insufficient resolution in the xy plane.

Ultimately, a final blend of 1% BAPO, 28% HMB, and 1% TiO$_2$ resulted in a successful scaffold build with an exposure time of 60 seconds and a desired layer thickness of 120 μm.

Figure 9:
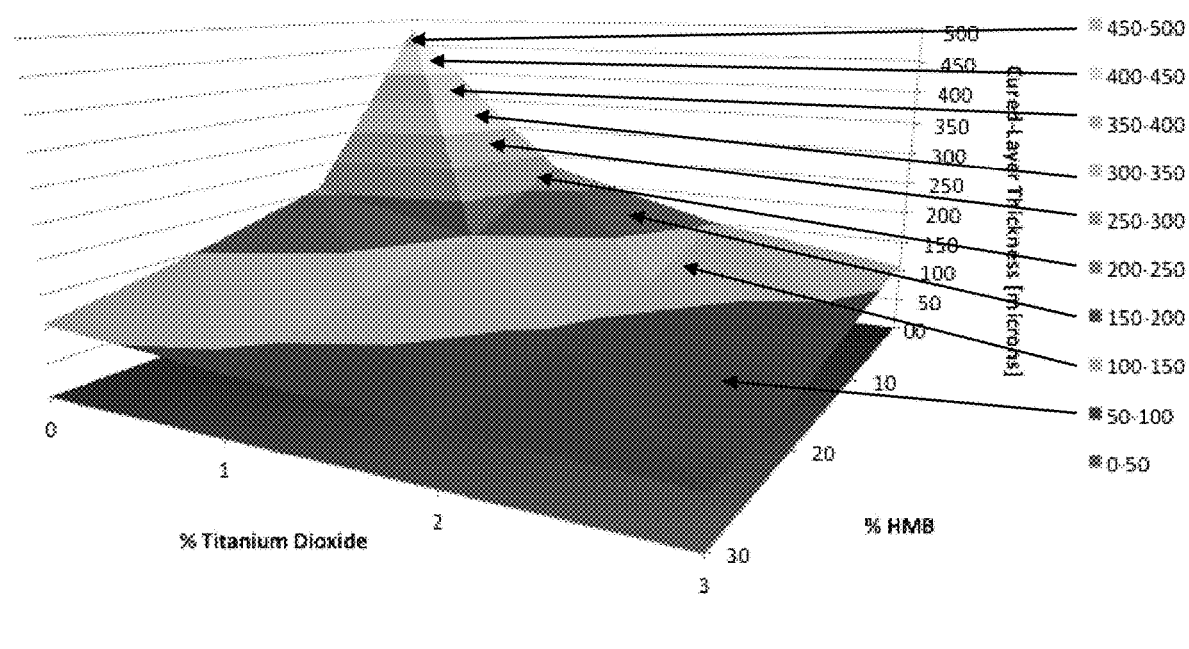
FIG. 9 illustrates a plot of the effects on cure layer thickness of a biocompatible resin using different percentages of titanium dioxide and oxybenzone at a fixed concentration of 1% BAPO.
Figure 10:
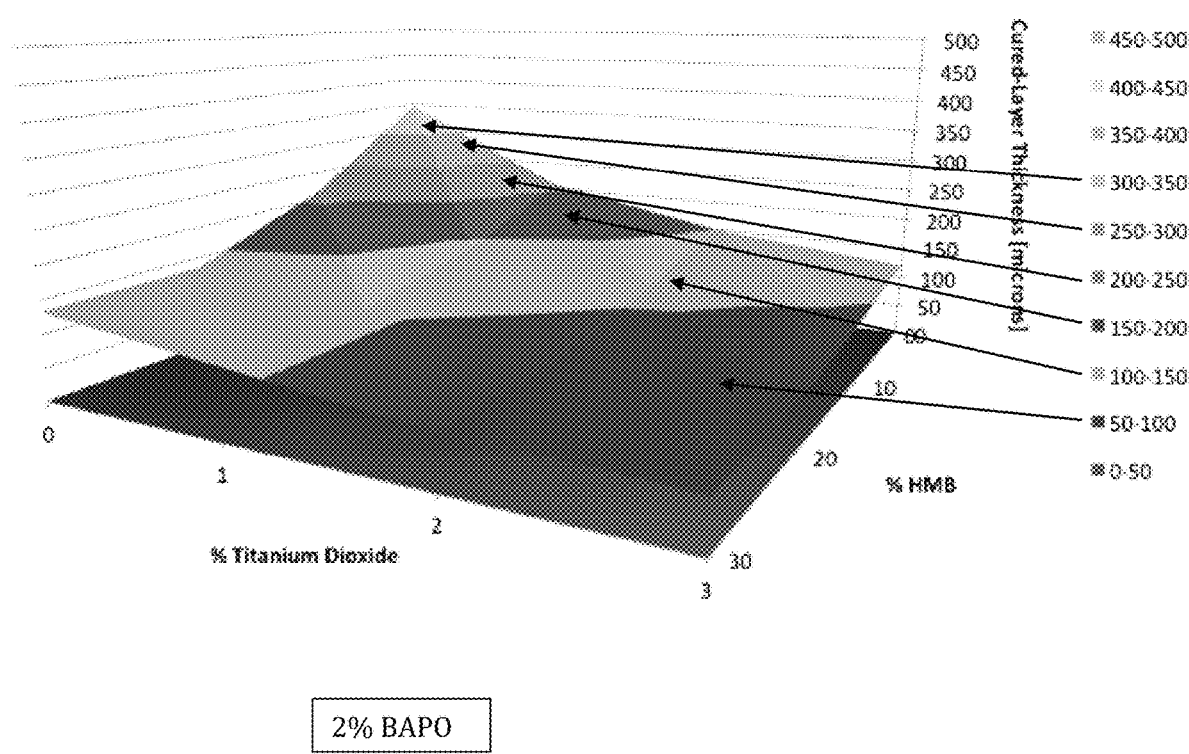
FIG. 10 illustrates a plot of the effects on cure layer thickness of a biocompatible resin using different percentages of titanium dioxide and oxybenzone at a fixed concentration of 2% BAPO.
Figure 11:
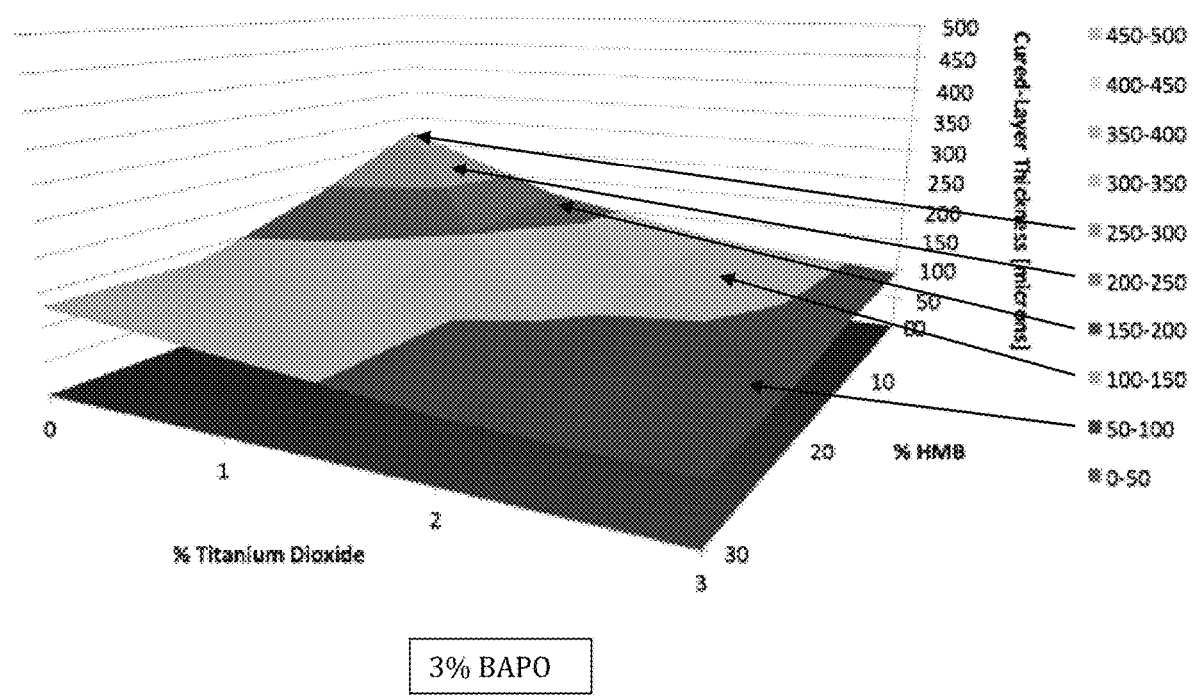
FIG. 11 illustrates a plot of the effects on cure layer thickness of a biocompatible resin using different percentages of titanium dioxide and oxybenzone at a fixed concentration of 3% BAPO.

These results were confirmed with follow-up cure tests, starting with 1% BAPO and 0% HMB, and increasing TiO$_2$ concentration from 0 to 3%. Five test cylinders were built at each test concentration, e.g. 5 tests with 1% BAPO, 0% HMB and 0% TiO$_2$, then the TiO$_2$ was increased to 1% and 5 cylinders were built, etc. Once 1% BAPO, 0% HMB and 3% TiO$_2$ was tested, the HMB was increased: 1% BAPO, 10% HMB, 0% TiO$_2$, and so on. As predicted, increasing the amount of BAPO from 1 to 3% reduced layer thickness, increasing TiO$_2$ increased dark cure but improved strength of the builds, the resulting builds at 3% TiO$_2$ frequently resisted breakage upon handling. Increasing the amount of oxybenzone decreased the dark cure created by the TiO$_2$. Potential successful build concentrations with no dark cure, good physical and qualitative properties (e.g. easily "peeled" or removed from the build platform, able to be handled fairly aggressively, and good strength) were exhibited with: (a) 2% BAPO, 30% HMB, and 0% to 2% TiO$_2$; 3% TiO$_2$ resulted in weaker builds, and (b) 1% BAPO, 30% HMB and 1-2% TiO$_2$. This confirmed the earlier run tests that resulted in successful scaffold builds at 1% BAPO, 28% HMB and 1% TiO$_2$. The results of the confirmatory tests are plotted in FIGS. 9 through 11.

Example 8

A Micro (EnvisionTEC, Inc., Dearborn, MI) printer at an intensity of 267 mW/dm2, an exposure time of 120 seconds was used to render 6 millimeter by 12 millimeter solid cylinders, with 50 micrometer thick layers. In this example, a photo-initiator package was used, with no added dye. 3% Irgacure® 819 (BASF [Ciba], Florham Park, NJ), and 3% Irgacure 784® (BASF [Ciba], Florham Park, NJ) by weight of each initiator to the weight of the PPF and DEF mixture was added to the polymer and solvent mixture which was in a weight ratio of PPF:DEF of 1.5:1.

Figure 12:
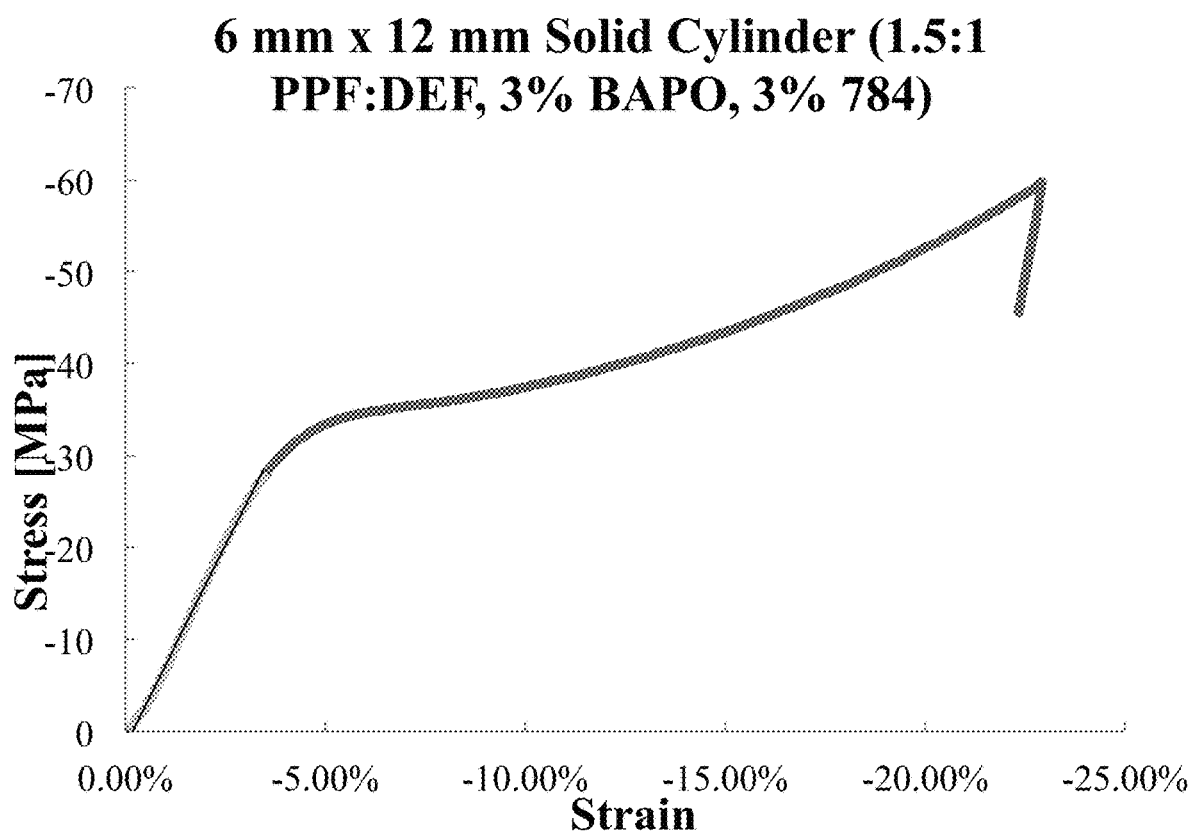
FIG. 12 plots stress versus strain of solid cylinders manufactured according to one embodiment of an additive manufacturing process.
Figure 13:
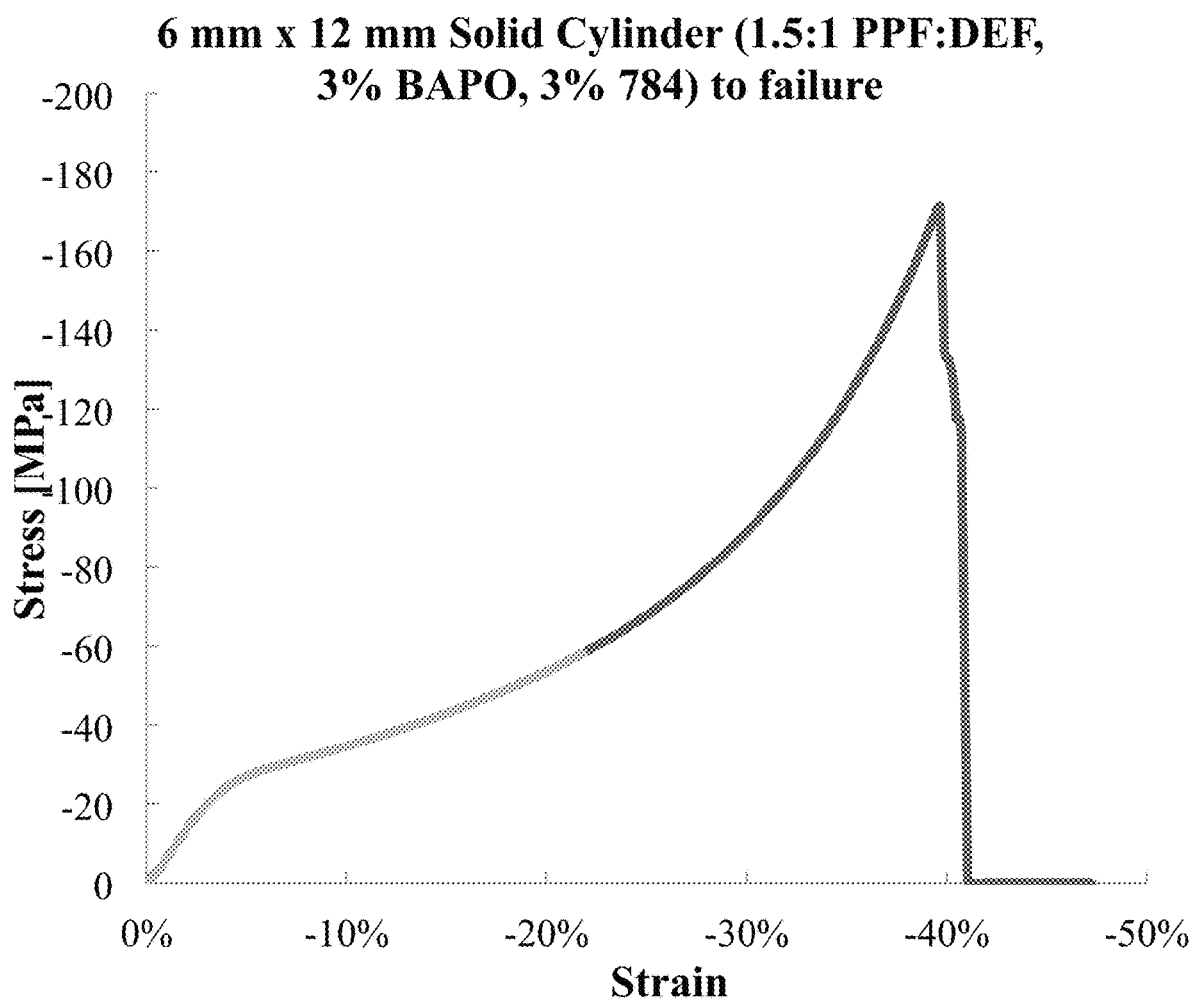
FIG. 13 plots the stress versus strain, to failure, of solid cylinders manufactured according to one embodiment of an additive manufacturing process.

The cylinders were printed and removed from the device. The strength of one of the cylinders was tested using Instron 8501 (Norwood, MA) with a load cell of 1000 lb$_f$ (4448N), strain rate of 0.1 mm/s and maximum strain of 2 mm. The cylinders exhibited a maximum modulus of elasticity of about 868 MPa at the linear portion of the graph. A plot of the stress versus strain of the cylinder is shown in FIG. 12. The strength of the same cylinder was tested to failure and exhibit an average modulus of 334 MPa. A plot of its stress versus strain to failure is shown in FIG. 13. Solid part manufacturing according to this Example could prove beneficial for tissue engineered devices that may undergo high compressive forces.

Example 9

In this example, as with Example 8, a photo-initiator package with no added dye was tested. A Perfactory P3 UV device was used at an intensity of 350 mW/dm2 and an exposure time of 30 seconds per layer to render porous cylindrical PPF scaffolds ("sleeves"). Target dimensions were: an outer diameter of approximately 2.75 mm, inner diameter of approximately 2.5 mm, approximately 6 mm height, wall thickness of about 125 µm, and pore size of about 350 µm. Final cylinder dimensions were slightly lower. Three percent Irgacure® 819 (BAPO) (BASF [Ciba], Florham Park, NJ) and 0.5% Irgacure® 784 (BASF [Ciba], Florham Park, NJ) (weight percents based on the combined weight of PPF and DEF) and diethyl fumarate were added to the primary material, PPF (for a resulting PPF:DEF ratio of 1:1) and used for scaffold production. No $TiO_2$ was used. The scaffolds were printed, removed from the cDLP device, and post-cured for 480 minutes in a UV light chamber (3D Systems ProCure). A compression test was conducted using an Instron 8501 (Norwood, MA) with a load cell of 100 $lb_f$ (444N), strain rate of 0.1 mm/s and maximum strain of 2 mm. The test was conducted on newly manufactured scaffolds, i.e. "green" scaffolds, and on post-cured scaffolds. The results showed an 1800% increase in elastic modulus with post-curing and a 2200% increase in compressive strength with post curing. FIGS. 6 and 7 illustrate these results.

Example 10

In this Example, the photo-initiator package of 3% Irgacure 819 (BASF Corp, Florham Park, NJ) and 3% Irgacure 784 (BASF Corp., Florham Park, NJ) (weight percents based on combined weight of polymer and solvent) was again tested, this time looking at the effect of exposure time on layer thickness and green strength of 3D printed parts. Interlayer strengths are important in assessing the overall strength of a printed part, and can only be tested in 3D printed parts, as opposed to single cured layers of PPF Or other resorbable polymer. DEF (Acros, Pittsburgh, PA) was heated in order to dissolve the Irgacures. The initiators and solvent were added to PPF (1200 Daltons PPF prepared as described in Example 1) to a 1.5:1.0 PPF/DEF ratio. Cure tests were run to produce layer thicknesses of 120, 150 and 180 µm. Exposure times at those thicknesses on a Perfactory Micro (EnvisionTEC, Inc.) at UV light intensity of about 195 mW/dm2 were 90, 180 and 210 seconds respectively. The build plate advanced 50 mm between each layer, resulting in overcuring over 70, 100 and 130 µm, respectively.

Solid PPF cylinders (6 mm length, 3 mm diameter) were designed in SolidWorks (Dassault Systems SolidWorks Corporation, Waltham, MA). This geometry was transferred to the Perfactory Micro. Three sets of cylinders were printed at 90 (N=2), 180 (N=7) and 210 (N=5) seconds, respectively. These parts were not post-cured so that the effect of exposure on the green strength of the parts could be tested. Compression testing was performed on an Instron 8501 (Norwood, MA) with a strain rate of 0.1 mm/s. The green strength, as defined by average modulus, of the parts printed at each exposure time is provided in Table 2.

TABLE 2

| Exposure Time (s) | Layer Thickness (µm) | Average Modulus (N) |
|---|---|---|
| 90 | 120 | 38.9 MPa (2) |
| 180 | 150 | 122.7 MPa (7) |
| 210 | 180 | 188.5 MPa (5) |

These data indicate exposure time affects layer thickness. Holding step size of overcuring (30 µm) constant, while allowing exposure time and overcuring depth to increase affects the green strength of a 3D rendered part. The strength of the parts held to the first group (120 µm layer thickness) is not below the level necessary for 3D printing but is significantly lower than the other two groups. At the low end of exposure time-green strength relationship (70 µm overcure and a 50 µm advance), reduced fabrication times and increased resolution was observed but also a risk of insufficient between-layer crosslinking to achieve satisfactory 3D printed scaffolds without delamination at some point during the build procedure. At the other end of the exposure-time green strength relationship, increased strength and build completion rates were observed but resolution in the cylinders was diminished.

Figure 14:
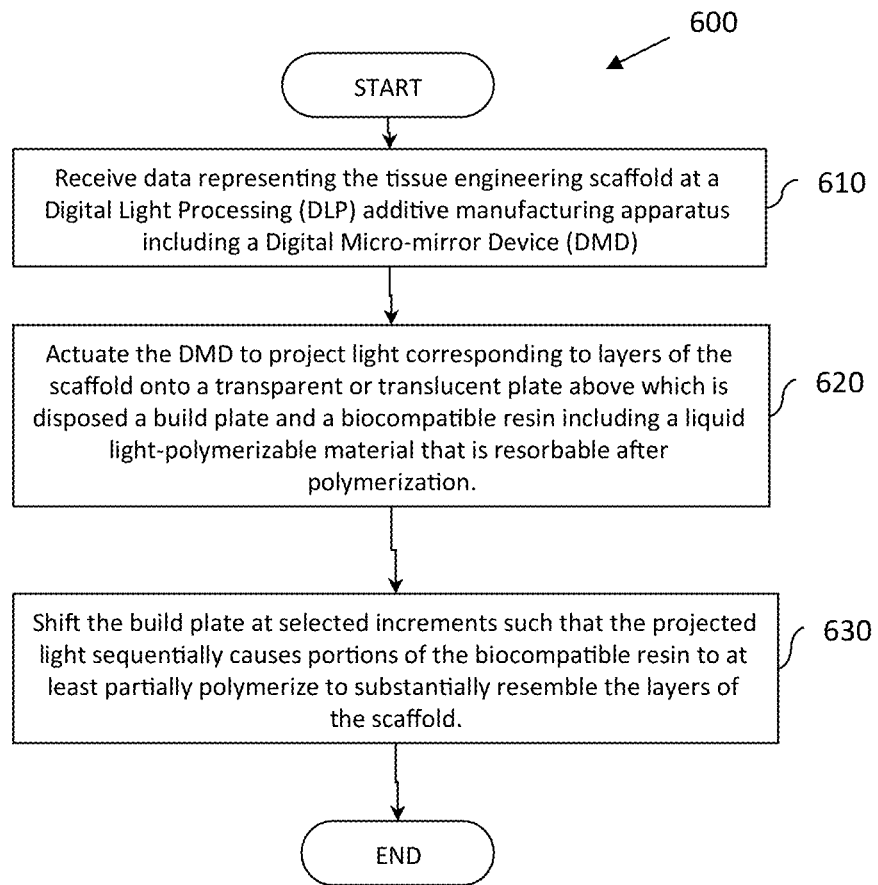
FIG. 14 illustrates a method of manufacturing a tissue engineering scaffold for implantation in a patient and promoting tissue growth.
Figure 15:
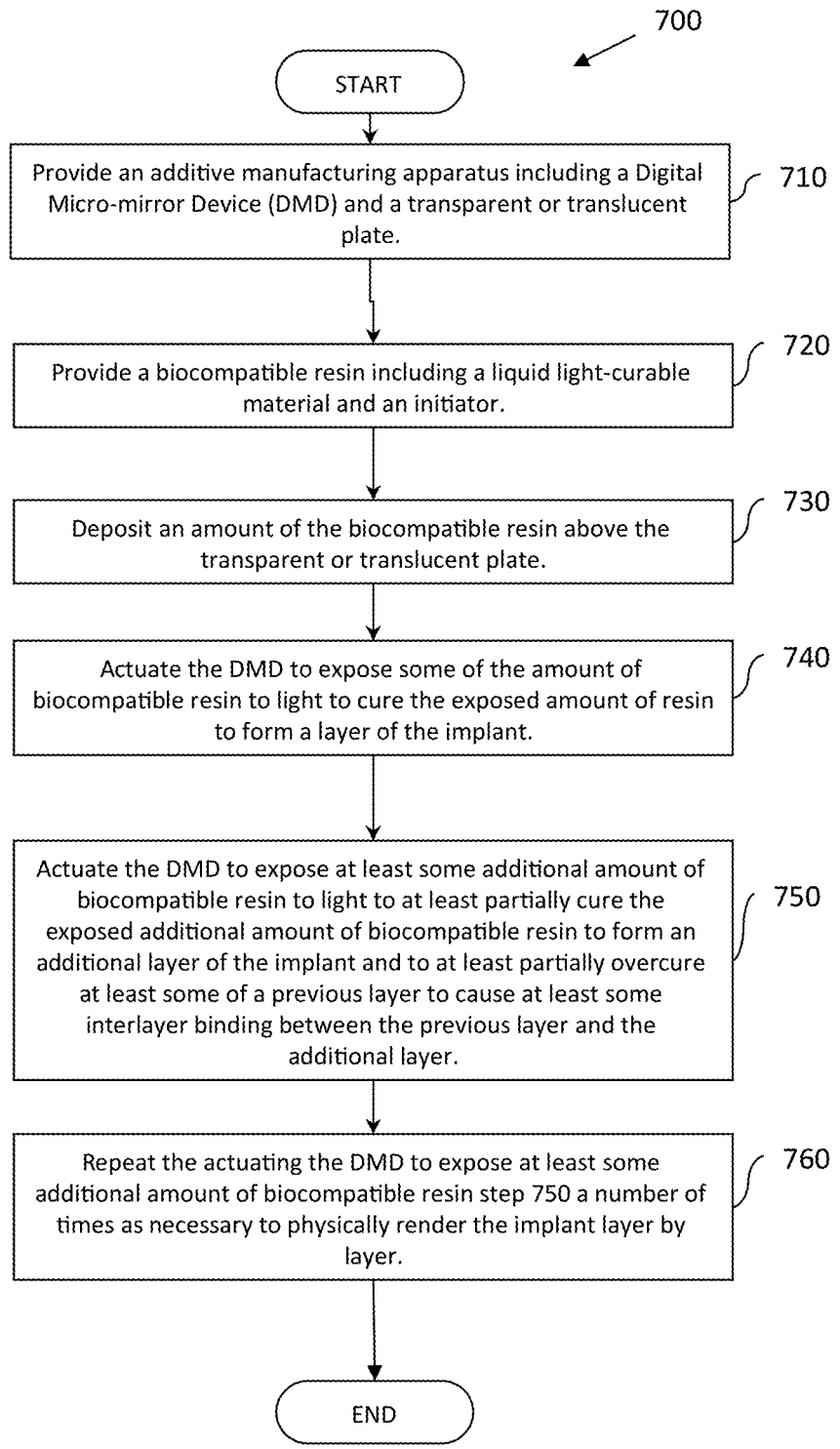
FIG. 15 illustrates a process for continuous digital light processing manufacturing of an implant to be implanted into a patient.

Example methods may be better appreciated with reference to the flow diagrams of FIGS. 14 and 15. While for purposes of simplicity of explanation, the illustrated methodologies are shown and described as a series of blocks, it is to be appreciated that the methodologies are not limited by the order of the blocks, as some blocks can occur in different orders or concurrently with other blocks from that shown or described. Moreover, less than all the illustrated blocks may be required to implement an example methodology. Furthermore, additional or alternative methodologies can employ additional, not illustrated blocks. While FIGS. 14 and 15 illustrate various actions occurring in serial, it is to be appreciated that various actions illustrated could occur substantially in parallel. While a number of processes are described, it is to be appreciated that a greater or lesser number of processes could be employed.

FIG. 14 illustrates a method 600 of manufacturing a tissue engineering scaffold for implantation in a patient and promoting tissue growth. The method 600 includes, at 610, receiving data representing the tissue engineering scaffold at a Digital Light Processing (DLP) additive manufacturing apparatus including a Digital Micromirror Device (DMD). At 620, the method 600 further includes actuating the DMD to project light corresponding to layers of the scaffold onto a transparent or translucent plate above which is disposed a build plate and a biocompatible resin including a liquid light-polymerizable material that is resorbable after polymerization. At 630, the method 600 further includes shifting the build plate at selected increments such that the projected light sequentially causes portions of the resin to at least partially polymerize to substantially resemble the layers of the scaffold.

FIG. 15 illustrates a process 700 for continuous digital light processing (cDLP) manufacturing of an implant to be implanted into a patient. The process 700 includes, at 710, providing an additive manufacturing apparatus including a Digital Micromirror Device (DMD) and a transparent or translucent plate. At 720, the process 700 further includes providing a biocompatible resin including a liquid light-curable material and an initiator. At 730, the process 700 further includes depositing an amount of the resin above the transparent or translucent plate. At 740, the process 700 further includes actuating the DMD to expose some of the amount of resin to light to cure the exposed amount of resin to form a layer of the implant. In one embodiment (not shown), the process 700 further includes shifting the rendered layer of the implant and depositing an additional amount of the resin above the transparent or translucent plate.

At 750, the process 700 further includes actuating the DMD to expose at least some additional amount of resin to light to at least partially cure the exposed additional amount of resin to form an additional layer of the implant and to at least partially overcure at least some of a previous layer to cause at least some interlayer binding between the previous layer and the additional layer. In one embodiment, the process 700 further includes shifting additional layers of the implant before depositing subsequent additional amounts of resin above the transparent or translucent plate, wherein at least one motor in the additive manufacturing apparatus causes the shifting to occur at increments of 75 micrometers or less. At 760, the process 700 further includes repeating the actuating the DMD to expose at least some additional amount of resin step 750 a number of times as necessary to physically render the implant layer by layer.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents. In all cases, the ranges are listed as approximate ranges with a variance around the boundaries of +/−5%. In other words, 20% should be read as "about 20%".

All references cited and discussed in this specification are incorporated herein by reference in their entirety.

What is claimed is:

1. A composition for a resin used in additive manufacturing of biocompatible medical devices comprising, a photo initiator, a light attenuator which limits transmission of light that activates the photo-initiator in a build direction of the additive manufacturing including by scattering at least some of the light in a second direction different from the build direction, and a light absorber which absorbs at least some of the light scattered in the second direction by the light attenuator, wherein the photo-initiator is an acylphosphine oxide, wherein the light absorber is one or more of a benzophenone, an oxybenzone, or an avobenzone.

2. The composition of claim 1 wherein the light attenuator is TiO2.

3. The composition of claim 1 wherein the photo-initiator is Bis(2,4,6-trimethylbenzoyl)-phenylphosphineoxide (BAPO).

4. The composition of claim 1 wherein the benzophenone is selected from the group consisting of: 2,4-dihydroxybenzophenone, 2,2',4,4'-tetrahydroxybenzophenone, sulisobenzone, sulixobenzone sodium, 2,2'-dihydroxy-4,4'-dimethyoxybenzophenone, 5-chloro-2-hydroxybenzophenone, dioxybenzone, sodium 2,2'-dihydroxy-4,4'-dimethoxybenzophenone-5,5'-disulfonate, 2-hydroxy -4-methoxy-4'-methyl-benzophenone, benzophenone-2, benzophenone-6, octabenzone, and 2-Hydroxy-4'-methoxybenzophenone (oxybenzone).

5. The composition of claim 1, wherein the light attenuator is Bis(.eta.5-2,4-cylcopentadien-1-yl)-bis(2,6-difluoro-3-(1H-pyrrol-1-yl)-phenyl) titanium.

6. The composition of claim 5, wherein the photo-initiator is Bis(2,4,6-trimethylbenzoyl)-phenylphosphineoxide (BAPO).

7. The composition of claim 6, wherein the light absorber is oxybenzone (2-Hydroxy-4-methoxybenzophenone).

8. The composition of claim 2 wherein the amount of TiO2 is 0.1 to 5.0% by weight of the polymer and solvent.

9. The composition of claim 3 wherein the amount of BAPO is 0.1 to 5.0% by weight of the polymer and solvent.

10. The composition of claim 1 wherein the amount of oxybenzone by weight of the polymer and solvent is about 25 to 35%.

11. The composition of claim 5 wherein the amount of Bis(.eta.5-2,4-cylcopentadien-1-yl)-bis(2,6-difluoro-3-(1H-pyrrol-1-yl)-phenyl) titanium by weight of the polymer and solvent is about 0.1 to 5.0%.

12. The composition of claim 6 wherein the amount of BAPO by weight of the polymer and solvent is about 0.1 to 5.0%.

13. The composition of claim 7 wherein the amount of oxybenzone by weight of the polymer and solvent is about 0.1 to 5.0%.

14. A resin composition used in additive manufacturing of a biocompatible medical device, comprising:
   a light attenuator in an amount by weight of the resin composition of about 0.1 to 5.0%,
   a photo-initiator in an amount by weight of the resin composition of about 0.1 to 5.0%, wherein the light attenuator is capable of limiting the transmission of light that activates the photo-initiator in a build direction of the additive manufacturing including by scattering at least some of the light in a second direction different from the build direction, and
   a light absorber in an amount by weight of the resin composition of about 5 to 25%, wherein the light absorber is capable of absorbing at least some of the light scattered in the second direction by the light attenuator,
   wherein the resin composition comprises at least one polymer and at least one solvent,
   further comprising a second light attenuator.

15. The resin composition of claim 14 wherein the light attenuator is titanium dioxide.

16. The resin composition of claim 14 wherein the photo-initiator is an acylphosphine oxide.

17. The resin composition of claim 16 wherein the photo-initiator is Bis(2,4,6-trimethylbenzoyl)-phenylphosphineoxide (BAPO).

18. The resin composition of claim 14 wherein the second light attenuator is Bis(.eta.5-2,4-cylcopentadien-1-yl)-bis(2,6-difluoro-3-(1H-pyrrol-1-yl)-phenyl) titanium.

19. The resin composition of claim 14 wherein the light absorber is a benzophenone.

20. The resin composition of claim 19 wherein the light absorber is oxybenzone (2-Hydroxy-4-methoxybenzophenone).

21. A light-polymerizable composition for use in additive manufacturing of biocompatible medical devices, comprising a biocompatible polymer, a solvent, and a biocompatible light attenuator in an amount of about 0.1-5% by weight of the polymer and solvent, a biocompatible photo-initiator in an amount of about 0.1-5% by weight of the polymer and solvent, and a biocompatible light absorber, wherein the biocompatible light attenuator limits transmission of light that activates the biocompatible photo-initiator in a build direction of the additive manufacturing including by scattering at least some of the light in a second direction different from the build direction, and the biocompatible light absorber absorbs at least some of the light scattered in the second direction by the biocompatible light attenuator, wherein the light absorber is a benzophenone, an oxybenzone, an avobenzone, or combinations thereof.

22. The light-polymerizable composition of claim 21, wherein the biocompatible light absorber is provided in an amount of about 10-35% by weight of the polymer and solvent.

23. The light-polymerizable composition of claim 21 further comprising a second light attenuator, wherein the second light attenuator is provided in an amount of about 0.1-5% by weight of the polymer and solvent.

24. The light-polymerizable composition of claim 23 wherein the second light attenuator is Bis(.eta.5-2,4-cylcopentadien-1-yl)-bis(2,6-difluoro-3-(1H-pyrrol-1-yl)-phenyl) titanium.

25. The light-polymerizable composition of claim 21 wherein the biocompatible polymer is polypropylene fumarate.

26. The light-polymerizable composition of claim 25 wherein the solvent is diethyl fumarate.

\* \* \* \* \*